(12) United States Patent
Chu et al.

(10) Patent No.: US 9,182,414 B2
(45) Date of Patent: *Nov. 10, 2015

(54) METHODS FOR IDENTIFYING A GLP-1 SECRETAGOGUE

(71) Applicant: Arena Pharmaceuticals, Inc., San Diego, CA (US)

(72) Inventors: Zhi-Liang Chu, San Diego, CA (US); James N. Leonard, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,866

(22) Filed: Nov. 19, 2012

(65) Prior Publication Data
US 2013/0078649 A1 Mar. 28, 2013

Related U.S. Application Data

(63) Continuation of application No. 11/919,381, filed as application No. PCT/US2006/016024 on Apr. 26, 2006, now Pat. No. 8,354,241.

(60) Provisional application No. 60/675,730, filed on Apr. 27, 2005.

(51) Int. Cl.
| | |
|---|---|
| G01N 33/567 | (2006.01) |
| G01N 33/68 | (2006.01) |
| A61K 31/40 | (2006.01) |
| A61K 31/403 | (2006.01) |
| A61K 31/405 | (2006.01) |
| A61K 31/4172 | (2006.01) |
| A61K 31/426 | (2006.01) |
| A61K 31/4439 | (2006.01) |
| A61K 31/445 | (2006.01) |
| A61K 31/497 | (2006.01) |
| A61K 31/4985 | (2006.01) |
| A61K 31/513 | (2006.01) |
| A61K 45/06 | (2006.01) |
| A61K 38/26 | (2006.01) |
| A61K 38/16 | (2006.01) |
| A61P 3/10 | (2006.01) |
| C07K 14/605 | (2006.01) |
| C07K 14/715 | (2006.01) |
| A61K 38/17 | (2006.01) |

(52) U.S. Cl.
CPC ............ *G01N 33/6893* (2013.01); *A61K 31/40* (2013.01); *A61K 31/403* (2013.01); *A61K 31/405* (2013.01); *A61K 31/4172* (2013.01); *A61K 31/426* (2013.01); *A61K 31/445* (2013.01); *A61K 31/4439* (2013.01); *A61K 31/497* (2013.01); *A61K 31/4985* (2013.01); *A61K 31/513* (2013.01); *A61K 45/06* (2013.01); *G01N 33/567* (2013.01); *A61K 38/177* (2013.01); *A61K 38/26* (2013.01); *C07K 14/605* (2013.01); *C07K 14/715* (2013.01); *G01N 2333/726* (2013.01); *G01N 2500/04* (2013.01); *G01N 2800/042* (2013.01)

(58) Field of Classification Search
None
See application file for complete search history.

(56) References Cited

FOREIGN PATENT DOCUMENTS

| WO | WO 01/68120 | 9/2001 |
|---|---|---|
| WO | WO 03/104196 | 12/2003 |
| WO | WO 2004/093785 | 11/2004 |
| WO | WO 2005/025554 | 3/2005 |
| WO | WO 2006/076231 | 7/2006 |

OTHER PUBLICATIONS

Weber et al (2003. J Med Chem. 46(10):1918-1930).*
Herrmann-Rinke et al (1996. Digestion. 57: 349-355).*
Anini et al., "Muscarinic receptors control glucagon-like peptide 1 secretion by human endocrine L cells," *Endocrinology*, 144(7):3244-3250 (2003).
Bork, *Genome Research*, 10:398 (2000).
Bose et al., "Glucagon-like peptide 1 can directly protect the heart against ischemia/reperfusion injury," *Diabetes*, 54:146-151 (2005).
Boyle et al., The design of a new potent and selective ligand for the orphan bombesin receptor subtype 3 (BRS3), *J. Pept. Sci.*, 11:136-141 (2005).
Brenner, *Trends in Genetics*, 15(4):132 (1999).
Doerks et al., *Trends in Genetics*, 14(6):248 (1998).
During et al., Glucagon-like peptide-1 receptor is involved in learning and neuroprotection, *Nat. Med.*, 9(9):1173-1179 (2003).
Fathi et al., *J. Cell Biochem Suppl.*, 24:237-246 (1996).
GenBank: AAA35604.1, "bombesin receptor subtype-3 [Homo sapiens]," (1993), [retrieved on Jan. 21, 2011]. Retrieved from the Internet: http://www.ncbi.nlm.nih.gov/protein/291877, 1 page.
GenBank: AY288423, "Mus musculus G protein-coupled receptor 119 (Gpr119) mRNA, complete cds," (2003), [retrieved on Jan. 21, 2011]. Retrieved from the Internet: http://www.ncbi.nlm.nih.gov/nuccore/32165529, 1 page.
Greig et al., "New therapeutic strategies and drug candidates for neurodegenerative diseases: p53 and TNF-alpha inhibitors, and GLP-1 receptor agonists," *Ann N.Y. Acad. Sci.*, 1035:290-315 (2004).
Holst et al., "The Incretin Approach for Diabetes Treatment—Modulation of Islet Hormone Release by GLP-1 Agonism," Diabetes, 53(3):S197-S204 (2004).

(Continued)

*Primary Examiner* — Zachary Howard
(74) *Attorney, Agent, or Firm* — Fish & Richardson P.C.

(57) ABSTRACT

The present invention concerns combination of an amount of a BRS-3 agonist with an amount of a dipeptidyl peptidase IV (DPP-IV) inhibitor such that the combination provides an effect in lowering a blood glucose level or in increasing a blood GLP-1 level in a subject over that provided by the amount of the BRS-3 agonist alone and by the amount of the DPP-IV inhibitor alone and the use of such a combination for treating or preventing obesity and diabetes and conditions related thereto and conditions ameliorated by increasing a blood GLP-1 level. The present invention also relates to the use of a G protein-coupled receptor to screen for GLP-1 secretagogues.

52 Claims, 2 Drawing Sheets

(56) References Cited

OTHER PUBLICATIONS

Katsuma et al., "Bile acids promote glucagon-like peptide-1 secretion through TGR5 in a murine enteroendocrine cell line STC-1,"*Biochem. Biophys. Res. Commun.*, 329:386-390 (2005).

Kaufman et al., *Blood*, 94:3178-3184 (1999).

Lammerich et al., "Identification and functional characterization of hemorphins VV-H-7 and LVV-H-7 as low-affinity agonists for the orphan bombesin receptor subtype 3," *Br. J. Pharmacol.*, 138:1431-1440 (2003).

Liu et al., *Biochemistry*, 41:8954-8960 (2002).

Liu et al., "bombesin receptor subtype-3 [Homo sapiens]," GenBank databases, NCBI, Accession No. NP_001718, Apr. 23, 2005 [online], [retrieved on Oct. 5, 2011]. Retrieved from the Internet: http://www.ncbi.nlm.nih.gov/protein/4502455?sat=34&satkey=13334563.

Mantey et al., Rational design of a peptide agonist that interacts selectively with the orphan receptor, bombesin receptor subtype 3, *J. Biol. Chem.*, 276(12):9219-9229 (2001).

Mantey et al., "Development of bombesin analogs with conformationally restricted amino acid substitutions with enhanced selectivity for the orphan receptor human bombesin receptor subtype 3," *J. Pharmacol. Exp. Ther.*, 310(3):1161-1170 (2004).

Mentlein, "Therapeutic assessment of glucagon-like peptide-1 agonists compared with dipeptidyl peptidase IV inhibitors as potential antidiabetic drugs," Expert Opin. Investig. Drugs, 14(1):57-64 (2005).

Mest et al., "Dipeptidyl peptidase inhibitors as new drugs for the treatment of type 2 diabetes," Diabetologia, 48(4):616-620 (2005).

Nakamichi et al., "Function of pancreatic β cells and adipocytes in bombesin receptor subtype-3-deficient mice," Biochemical Research and Biophysical Research Communications, 318:698-703 (2004).

Nash et al., "Synaptic activity augments muscarinic acetylcholine receptor-stimulated inositol 1,4,5-trisphosphate production to facilitate Ca2+ release in hippocampal neurons," *J. Biol. Chem.*, 279(47):49036-49044 (2004).

Nauck et al., "Incretins and their analogues as new antidiabetic drugs," *Drug News Perspect*, 16(7):413-422 (2003).

Nauck et al., "Gastric inhibitory polypeptide and glucagon-like peptide-1 in the pathogenesis of type 2 diabetes," *Diabetes*, 53(Suppl. 3):S190-S196 (2004).

Ngo et al., "The Protein Folding Problem and Tertiary Structure Prediction, Chapter 14: Computational Complexity Protein Structure Prediction, and the Levinthal Paradox," pp. 433-440 and 492-495 only (1994).

Ohki-Hamazaki et al., "Mice lacking bombesin receptor subtype-3 develop metabolic defects and obesity," *Nature*, 390:165-169 (1997).

Reubi et al., *Eur. J. Nucl. Med. Mol. Imaging*, 30(5):781-793 (2003).

Ryan et al., "Ability of various bombesin receptor agonists and antagonists to alter intracellular signaling of the human orphan receptor BRS-3," *J. Biol. Chem.*, 273(22):13613-13624 (1998).

Skolnick et al., *Trends in Biotech*, 18(1):34 (2000).

Wada et al., Frontiers in Gastroenterology, 5(3):324-330 (2000).

Wang et al., *Nuc. Acids Res.*, 27:4609-4618 (1999).

Wasada, T., "Glucagon-like peptide-1 (GLP-1)," Nippon Rinsho, 62(6):1175-1180 (2004).

Weber et al., "Design of selective peptidomimetic agonists for the human orphan receptor BRS-3," *J. Med. Chem.*, 46:1918-1930 (2003).

Wells, *Biochemistry*, 29(37):8509-8517 (1990).

Zander et al., "Effect of 6-week course of glucagon-like peptide 1 on glycaemic control, insulin sensitivity, and beta-cell function in type 2 diabetes: a parallel-group study," *Lancet*, 359:824-830 (2002).

* cited by examiner

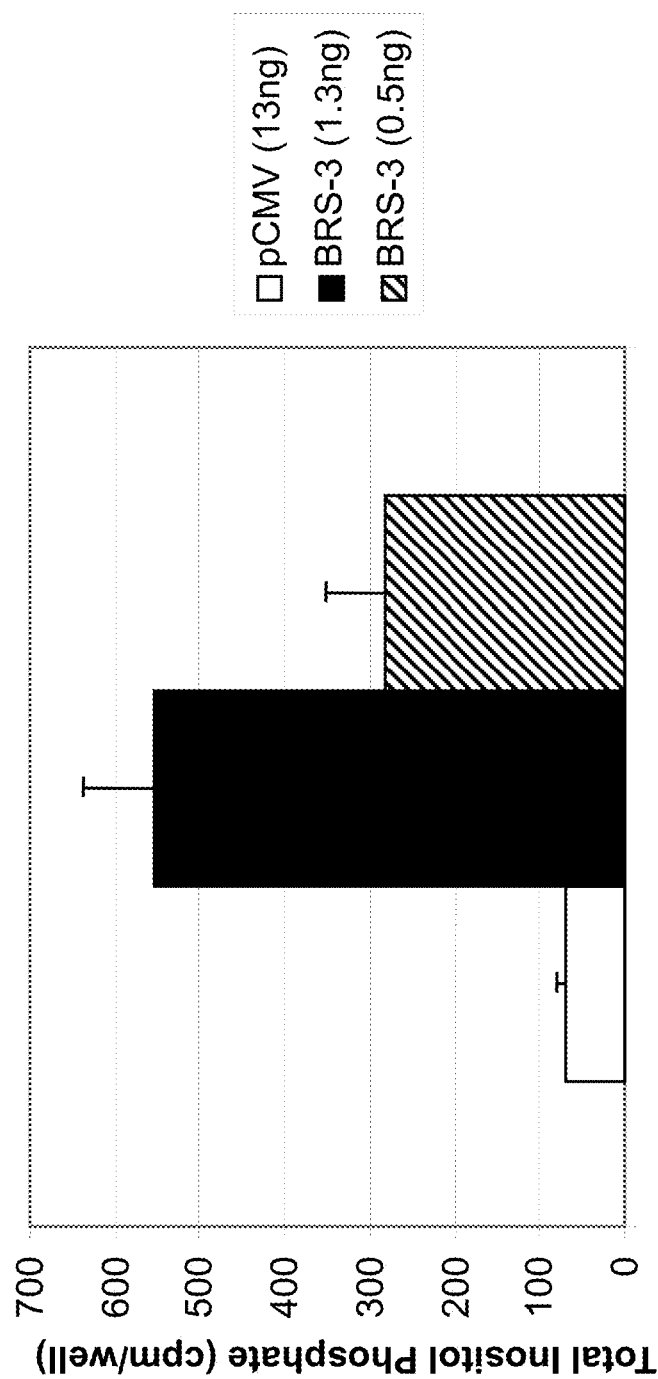
Figure 1. IP3 Assay in COS-7 Cells

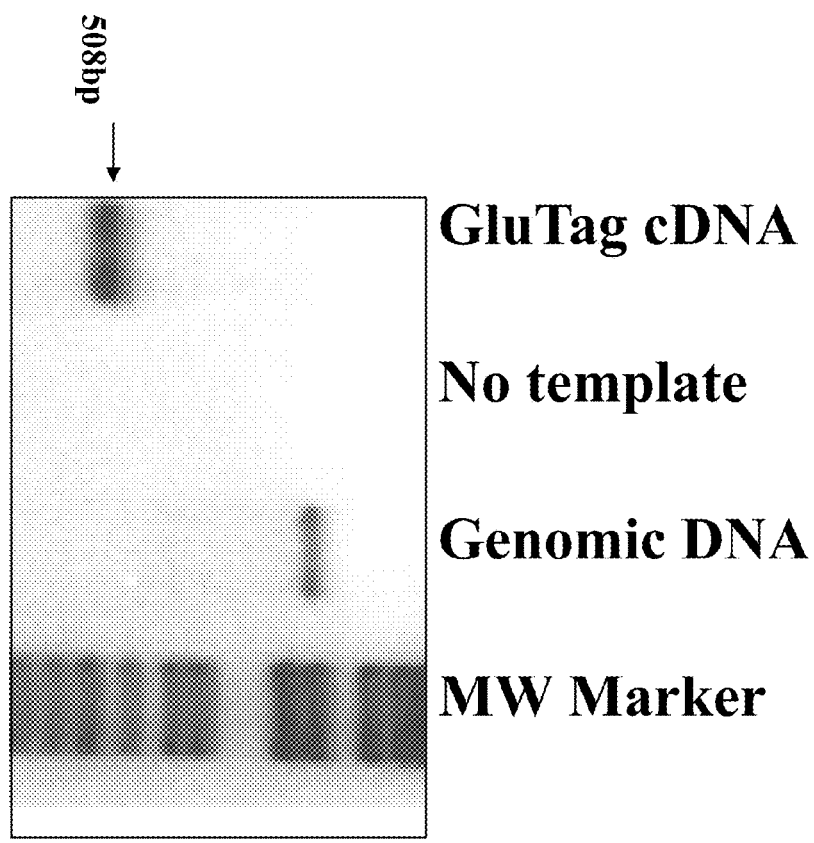
Figure 2. Expression of BRS-3 in GLUTag Cells

METHODS FOR IDENTIFYING A GLP-1 SECRETAGOGUE

CROSS-REFERENCE TO RELATED APPLICATIONS

This application is a continuation of U.S. patent application Ser. No. 11/919,381, filed on Jul. 31, 2009 (now U.S. Pat. No. 8,354,241), which is a 371 of PCT/US2006/016024, filed on Apr. 26, 2006, and which claims priority to U.S. Provisional Appl. No. 60/675,730, filed on Apr. 27, 2005. All of the above-referenced applications are hereby incorporated by reference.

FIELD OF THE INVENTION

The present invention relates to compositions and methods for treating or preventing obesity and diabetes and conditions related thereto. The present invention further relates to compositions and methods for increasing a blood GLP-1 level in a mammal. The present invention also relates to methods of using a G protein-coupled receptor to screen for GLP-1 secretagogues.

BACKGROUND OF THE INVENTION

The following discussion is intended to facilitate the understanding of the invention, but is not intended nor admitted to be prior art to the invention.

A. Obesity and Diabetes

Obesity is the most common metabolic disease in developed nations. Despite public health education and initiatives, its prevalence continues to rise, with greater than 30% of adults in the United States being obese and greater than 60% of adults being overweight or obese. The World Health Organization has estimated that worldwide, over one billion adults are overweight, with at least 300 million of them being obese. Obesity leads to, or significantly increases the risk of, a wide range of comorbidities that includes but is not limited to hypertension, congestive cardiomyopathy, coronary heart disease, stroke, dyslipidemia, metabolic syndrome, and Type 2 diabetes [Bays, Obesity Research (2004) 12:11971211] and premature death. There is an unmet medical need for safe and effective antiobesity drugs as a therapeutic option with which to reduce the worldwide obesity epidemic.

The incidence of Type 2 diabetes in the United States is about 7% and accounts for as much as 10% of all health care dollars. Furthermore, the incidence of Type 2 diabetes worldwide is increasing such that Type 2 diabetes is now considered to be a worldwide epidemic. Type 2 diabetes is characterized by fasting and postprandial hyperglycemia and by relative insulin insufficiency. Hyperglycemia may cause long-term microvascular and macrovascular complications, such as nephropathy, neuropathy, retinopathy, and peripheral vascular disease. In addition, Type 2 diabetes is a comorbid disease that frequently compounds hyperlipidemia, atherosclerosis and hypertension. Hyperlipidemia is a primary risk factor for cardiovascular disease due to atherosclerosis. Type 2 diabetes causes significant morbidity and mortality at considerable expense to patients, their families and society.

B. Glucagon-Like Peptide-1 (GLP-1)

Glucagon-like peptide-1 (GLP-1) is an incretin hormone derived from the posttranslaltional modification of proglucagon and secreted by gut endocrine cells. GLP-1 mediates its actions through a specific G protein-coupled receptor (GPCR), namely GLP-1R. GLP-1 is best characterized as a hormone that regulates glucose homeostasis. GLP-1 has been shown to stimulate glucose-dependent insulin secretion and to increase pancreatic beta cell mass. GLP-1 has also been shown to reduce the rate of gastric emptying and to promote satiety. The efficacy of GLP-1 peptide agonists in controlling blood glucose in Type 2 diabetics has been demonstrated in several clinical studies [see, e.g., Nauck et al., Drug News Perspect (2003) 16:413-422], as has its efficacy in reducing body mass [Zander et al., Lancet (2002) 359:824-830].

GLP-1 receptor agonists are additionally useful in protecting against myocardial infarction and against cognitive and neurodegenerative disorders. GLP-1 has been shown to be cardioprotective in a rat model of myocardial infarction [Bose et al., Diabetes (2005) 54:146-151], and GLP-1R has been shown in rodent models to be involved in learning and neuroprotection [During et al., Nat Med (2003) 9:1173-1179; and Greig et al., Ann NY Acad Sci (2004) 1035:290-315].

Certain disorders such as Type 2 diabetes are characterized by a deficiency in GLP-1 [see, e.g., Nauck et al., Diabetes (2004) 53 Suppl 3:S190-196].

Current GLP-1 peptide agonists suffer from a lack of oral bioavailability, negatively impacting patient compliance. Efforts to develop orally bioavailable non-peptidergic, small-molecule agonists of GLP-1R have so far been unsuccessful [Mentlein, Expert Opin Investig Drugs (2005) 14:57-64]. An attractive alternative approach is to develop an orally active composition for increasing an endogenous level of GLP-1 in the blood.

C. BRS-3

Bombesin is a 14 amino acid peptide isolated from frog skin. Bombesin Receptor Subtype-3 BRS-3 G protein-coupled receptor (BRS-3; e.g., human BRS-3, GenBank® Accession No. AAA35604 and alleles thereof; e.g., mouse BRS-3, GenBank® Accession No. AY288423 and alleles thereof) exhibits about 50% homology to gastric-releasing peptide receptor (GRP-R) and neuromedin B receptor (NMB-R), and together they form the bombesin-like receptor group. BRS-3 is selectively expressed in tissues including hypothalamus and uterus. BRS-3 activation leads to increased accumulation of intracellular inositol 1,4,5-triphosphate (IP3), consistent with BRS-3 being coupled to Gq. In recent studies, BRS-3 knockout mice developed obesity, diabetes, and hypertension [Ohki-Hamazaki et al., Nature (1997) 390: 165-169].

D. Dipeptidyl Peptidase IV (DPP-IV)

Dipeptidyl peptidase IV (DPP-IV, EC 3.4.14.5) exhibits catalytic activity against a broad range of peptide substrates that includes peptide hormones, neuropeptides, and chemokines. The incretins glucagon-like peptide 1 (GLP-1) and glucose-dependent insulinotropic polypeptide (GIP), which stimulate glucose-dependent insulin secretion and otherwise promote blood glucose homeostasis, are rapidly cleaved by DPP-IV at the position 2 alanine leading to inactivation of their biological activity. Both pharmacological and genetic attenuation of DPP-IV activity is associated with enhanced incretin action, increased insulin, and lower blood glucose in vivo. Genetic attenuation of DPP-IV activity has been shown to provide resistance to obesity and to improve insulin sensitivity. A second-generation DPP-IV inhibitor, LAF237 (Ahren et al., J Clin Endocrinol Metab (2004) 89:2078-2084; and Villhauer et al., J Med Chem (2003) 46:2774-2789; the disclosure of each of which is herein incorporated by reference in its entirety), is currently in phase 3 clinical trials for Type 2 diabetes and additional DPP-IV inhibitors are in clinical development.

Because the incretin hormones are not the only substrates for DPP-IV, there is concern that inhibition of the cleavage of other endogenous DPP-IV substrates may give rise to undesirable side effects [see, e.g., Chen et al, J Biol Regul Homeost Agents (2004) 18:47-54, the disclosure of which is herein incorporated by reference in its entirety]. It therefore would be advantageous to identify an activity promoting blood glucose homeostasis which is associated with substantially lower concentrations of DPP-IV inhibitor.

E. G Protein-Coupled Receptors

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an agonist binds to a G protein-coupled receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 Life Sciences 1095 (1988). Although other G proteins may exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition.

Gs stimulates the enzyme adenylyl cyclase. Gi (and Gz and Go), on the other hand, inhibit adenylyl cyclase. Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, From Neuron To Brain ($3^{rd}$ Ed.) Nichols, J. G. et al eds. Sinauer Associates, Inc. (1992). Thus, assays that detect cAMP can be utilized to determine if a candidate compound is, e.g., an agonist to a Gs-associated receptor (i.e., such a compound would increase the levels of cAMP). Gq and Go are associated with activation of the enzyme phospholipase C, which in turn hydrolyzes the phospholipid $PIP_2$, releasing two intracellular messengers: diacyclglycerol (DAG) and inositol 1,4,5-triphosphate (IP3). Increased accumulation of IP3 is associated with activation of Gq- and Go-associated receptors. See, generally, "Indirect Mechanisms of Synaptic Transmission," Chpt. 8, From Neuron To Brain ($3^{rd}$ Ed.) Nichols, J. G. et al eds. Sinauer Associates, Inc. (1992). Assays that detect IP3 accumulation can be utilized to determine if a candidate compound is, e.g., an agonist to a Gq- or Go-associated receptor (i.e., such a compound would increase the levels of IP3). Assays that detect the level of intracellular free calcium can also be utilized to determine if a candidate compound is, e.g., an agonist to a Gq or Go-associated receptor (i.e., such a compound would increase the levels of intracellular free calcium).

See, e.g., Table A ("N/A": "not applicable").

TABLE A

| G protein | Effect on cAMP Production upon Activation of GPCR (i.e., constitutive activation or agonist binding) | Effect on IP3 Accumulation upon Activation of GPCR (i.e., constitutive activation or agonist binding) | Effect on cAMP Production upon contact with an Inverse Agonist | Effect on IP3 Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

There are also promiscuous G proteins, which appear to couple several classes of GPCRs to the phospholipase C pathway, such as $G\alpha15$ or $G\alpha16$ [Offermanns & Simon, J Biol Chem (1995) 270:15175-80], or chimeric G proteins designed to couple a large number of different GPCRs to the same pathway, e.g. phospholipase C [Milligan & Rees, Trends in Pharmaceutical Sciences (1999) 20:118-24]. Assays that detect the level of intracellular free calcium can be utilized to determine if a candidate compound is, e.g., an agonist to a GPCR coupled to the phospholipase C pathway (i.e., such a compound would increase the levels of intracellular free calcium).

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation." An endogenous receptor exhibiting activity in the absence of ligand is referred to as a constitutively active endogenous receptor.

SUMMARY OF THE INVENTION

The present invention concerns combination of an amount of a BRS-3 agonist with an amount of a dipeptidyl peptidase IV (DPP-IV) inhibitor such that the combination provides an effect in lowering a blood glucose level in a subject over that provided by the amount of the BRS-3 agonist or the amount of the DPP-IV inhibitor alone and the use of such a combination for treating or preventing diabetes and conditions related thereto. The present invention further concerns combination of an amount of a BRS-3 agonist with an amount of a dipeptidyl peptidase IV (DPP-IV) inhibitor such that the combination provides an effect in increasing a blood GLP-1 level in a subject over that provided by the amount of the BRS-3 agonist or the amount of the DPP-IV inhibitor alone and the use of such a combination for treating or preventing a condition ameliorated by increasing a blood GLP-1 level or for increasing a blood GLP-1 level in a subject deficient in GLP-1. The present invention also relates to methods of using BRS-3 G protein-coupled receptor to screen for GLP-1 secretagogues.

In a first aspect, the present invention features a method of treating or preventing diabetes or a condition related thereto comprising administering to a subject in need thereof a therapeutically effective amount of a composition comprising or consisting essentially of a BRS-3 agonist and a DPP-IV inhibitor. In certain embodiments, the BRS-3 agonist and the DPP-IV inhibitor are administered in amounts sufficient to lower a blood glucose level in the subject. In certain embodiments, the blood glucose level is an elevated blood glucose level.

The present invention additionally features a method of reducing body mass comprising administering to a subject in need thereof a therapeutically effective amount of a composition comprising or consisting essentially of a BRS-3 agonist and a DPP-IV inhibitor. In certain embodiments, the BRS-3 agonist and the DPP-IV inhibitor are administered in amounts sufficient to increase a blood GLP-1 level in the subject. In certain embodiments, the subject in need thereof has a BMI of 27 or greater. In certain embodiments, the subject in need thereof is overweight. In certain embodiments, the subject in need thereof is obese.

The present invention additionally features a method of treating or preventing obesity or a condition related thereto comprising administering to a subject in need thereof a therapeutically effective amount of a composition comprising or consisting essentially of a BRS-3 agonist and a DPP-IV inhibitor. In certain embodiments, the BRS-3 agonist and the DPP-IV inhibitor are administered in amounts sufficient to increase a blood GLP-1 level in the subject.

The present invention additionally features a method of treating or preventing a condition ameliorated by increasing a blood GLP-1 level comprising administering to a subject in need thereof a therapeutically effective amount of a composition comprising or consisting essentially of a BRS-3 agonist and a DPP-IV inhibitor. In certain embodiments, the BRS-3 agonist and the DPP-IV inhibitor are administered in amounts sufficient to increase a blood GLP-1 level in the subject.

The present invention additionally features a method of increasing a blood GLP-1 level comprising administering to a subject deficient in GLP-1 a therapeutically effective amount of a composition comprising or consisting essentially of a BRS-3 agonist and a DPP-IV inhibitor. In certain embodiments, the BRS-3 agonist and the DPP-IV inhibitor are administered in amounts sufficient to increase a blood GLP-1 level in the subject.

In certain embodiments, diabetes is Type 2 diabetes.

In certain embodiments, the condition related to diabetes is selected from the group consisting of hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity.

In certain embodiments, the condition related to obesity is selected from the group consisting of hypertension, congestive cardiomyopathy, varicosities, pulmonary embolism, coronary heart disease, stroke, idiopathic intracranial hypertension, meralgia paresthetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, Type 2 diabetes, dyslipidemia, hyperandrogenemia in women, polycystic ovarian syndrome, dysmenorrhea, infertility, pregnancy complications, and male hypogonadism. In certain embodiments, the condition related to obesity is selected from the group consisting of hypertension, congestive cardiomyopathy, coronary heart disease, stroke, dyslipidemia, metabolic syndrome, and Type 2 diabetes.

In certain embodiments, the condition ameliorated by increasing a blood GLP-1 level is selected from the group consisting of diabetes, a condition related to diabetes, myocardial infarction, learning impairment, memory impairment, and a neurodegenerative disorder. In certain embodiments, the condition ameliorated by increasing a blood GLP-1 level is a neurodegenerative disorder selected from the group consisting of excitotoxic brain damage caused by severe epileptic seizures, Alzheimer's disease, Parkinson's disease, Huntington's disease, prion-associated disease, stroke, motor-neuron disease, learning or memory impairment, traumatic brain injury, spinal cord injury, and peripheral neuropathy.

In certain embodiments, the subject is a human.

In a second aspect, the present invention features a composition comprising or consisting essentially of a BRS-3 agonist and a DPP-IV inhibitor. In certain embodiments, the present invention relates to a dosage form of the composition wherein the BRS-3 agonist and the DPP-IV inhibitor are in amounts sufficient to lower a blood glucose level in a subject. In certain embodiments, the blood glucose level is an elevated blood glucose level. In certain embodiments, the present invention relates to a dosage form of the composition wherein the BRS-3 agonist and the DPP-IV inhibitor are in amounts sufficient to increase a blood GLP-1 level in a subject.

In certain embodiments, the subject is a human.

In a third aspect, the present invention features a composition comprising or consisting essentially of a BRS-3 agonist and a DPP-IV inhibitor for use in a method of treatment of the human or animal body by therapy. In certain embodiments, the present invention relates to a dosage form of the composition wherein the BRS-3 agonist and the DPP-IV inhibitor are in amounts sufficient to lower a blood glucose level in a subject. In certain embodiments, the blood glucose level is an elevated blood glucose level. In certain embodiments, the present invention relates to a dosage form of the composition wherein the BRS-3 agonist and the DPP-IV inhibitor are in amounts sufficient to increase a blood GLP-1 level in a subject.

The present invention additionally features a composition comprising or consisting essentially of a BRS-3 agonist and a DPP-IV inhibitor for use in a method of treatment or prevention of diabetes or a condition related thereto of the human or animal body by therapy. In certain embodiments, the present invention relates to a dosage form of the composition wherein the BRS-3 agonist and the DPP-IV inhibitor are in amounts sufficient to lower a blood glucose level in a subject. In certain embodiments, the blood glucose level is an elevated blood glucose level.

The present invention additionally features a composition comprising or consisting essentially of a BRS-3 agonist and a DPP-IV inhibitor for use in a method of reducing body mass of the human or animal body by therapy. In certain embodiments, the present invention relates to a dosage form of the composition wherein the BRS-3 agonist and the DPP-IV inhibitor are in amounts sufficient to increase a blood GLP-1 level in a subject.

The present invention additionally features a composition comprising or consisting essentially of a BRS-3 agonist and a DPP-IV inhibitor for use in a method of treatment or prevention of obesity or a condition related thereto of the human or animal body by therapy. In certain embodiments, the present invention relates to a dosage form of the composition wherein the BRS-3 agonist and the DPP-IV inhibitor are in amounts sufficient to increase a blood GLP-1 level in a subject.

The present invention additionally features a composition comprising or consisting essentially of a BRS-3 agonist and a DPP-IV inhibitor for use in a method of treatment or prevention of a condition ameliorated by increasing a blood GLP-1 level of the human or animal body by therapy. In certain embodiments, the present invention relates to a dosage form of the composition wherein the BRS-3 agonist and the DPP-IV inhibitor are in amounts sufficient to increase a blood GLP-1 level in a subject.

The present invention additionally features a composition comprising or consisting essentially of a BRS-3 agonist and a DPP-IV inhibitor for use in a method of treatment or prevention of a deficiency of GLP-1 of the human or animal body by therapy. In certain embodiments, the present invention relates to a dosage form of the composition wherein the BRS-3 agonist and the DPP-IV inhibitor are in amounts sufficient to increase a blood GLP-1 level in a subject.

In certain embodiments, the subject is a human.

In a fourth aspect, the present invention features a method of preparing a pharmaceutical composition, said method comprising or consisting essentially of admixing a BRS-3 agonist and a DPP-IV inhibitor, together with at least one pharmaceutically acceptable carrier. In certain embodiments, the method further comprises the step of preparing a dosage form of the pharmaceutical composition wherein the BRS-3 agonist and the DPP-IV inhibitor are in amounts sufficient to lower a blood glucose level in a subject. In certain embodiments, the blood glucose level is an elevated blood glucose level. In certain embodiments, the method further comprises the step of preparing a dosage form of the pharmaceutical composition wherein the BRS-3 agonist and the DPP-IV inhibitor are in amounts sufficient to increase a blood GLP-1 level in a subject.

In certain embodiments, the subject is a human.

In a fifth aspect, the present invention features a pharmaceutical composition comprising or consisting essentially of a BRS-3 agonist and a DPP-IV inhibitor, together with at least one pharmaceutically acceptable carrier. In certain embodiments, the present invention relates to a dosage form of the pharmaceutical composition wherein the BRS-3 agonist and the DPP-IV inhibitor are in amounts sufficient to lower a blood glucose level in a subject. In certain embodiments, the blood glucose level is an elevated blood glucose level. In certain embodiments, the present invention relates to a dosage form of the pharmaceutical composition wherein the BRS-3 agonist and the DPP-IV inhibitor are in amounts sufficient to increase a blood GLP-1 level in a subject.

In certain embodiments, the subject is a human.

In a sixth aspect, the present invention features a method of treating or preventing diabetes or a condition related thereto comprising administering to a subject in need thereof a therapeutically effective amount of a pharmaceutical composition in accordance with the fifth aspect. In certain embodiments, the BRS-3 agonist and the DPP-IV inhibitor are administered in amounts sufficient to lower a blood glucose level in the subject. In certain embodiments, the blood glucose level is an elevated blood glucose level. In certain embodiments, the BRS-3 agonist and the DPP-IV inhibitor are administered in amounts sufficient to increase a blood GLP-1 level in the subject.

The present invention additionally features a method of reducing body mass comprising administering to a subject in need thereof a therapeutically effective amount of a pharmaceutical composition in accordance with the fifth aspect. In certain embodiments, the BRS-3 agonist and the DPP-IV inhibitor are administered in amounts sufficient to increase a blood GLP-1 level in the subject. In certain embodiments, the subject in need thereof has a BMI of 27 or greater. In certain embodiments, the subject in need thereof is overweight. In certain embodiments, the subject in need thereof is obese.

The present invention additionally features a method of treating or preventing obesity or a condition related thereto comprising administering to a subject in need thereof a therapeutically effective amount of a pharmaceutical composition in accordance with the fifth aspect. In certain embodiments, the BRS-3 agonist and the DPP-IV inhibitor are administered in amounts sufficient to increase a blood GLP-1 level in the subject.

The present invention additionally features a method of treating or preventing a condition ameliorated by increasing a blood GLP-1 level comprising administering to a subject in need thereof a therapeutically effective amount of a pharmaceutical composition in accordance with the fifth aspect. In certain embodiments, the BRS-3 agonist and the DPP-IV inhibitor are administered in amounts sufficient to increase a blood GLP-1 level in the subject.

The present invention additionally features a method of increasing a blood GLP-1 level comprising administering to a subject deficient in GLP-1 a therapeutically effective amount of a pharmaceutical composition in accordance with the fifth aspect. In certain embodiments, the BRS-3 agonist and the DPP-IV inhibitor are administered in amounts sufficient to increase a blood GLP-1 level in the subject.

In certain embodiments, the subject is a human.

In a seventh aspect, the present invention features use of a composition comprising or consisting essentially of a BRS-3 agonist and a DPP-IV inhibitor for the manufacture of a medicament for the treatment or prevention of diabetes or a condition related thereto. In certain embodiments, the present invention relates to a dosage form of the medicament wherein the BRS-3 agonist and the DPP-IV inhibitor are in amounts sufficient to lower a blood glucose level in a subject. In certain embodiments, the blood glucose level is an elevated blood glucose level. In certain embodiments, the present invention relates to a dosage form of the medicament wherein the BRS-3 agonist and the DPP-IV inhibitor are in amounts sufficient to increase a blood GLP-1 level in a subject.

The present invention additionally features use of a composition comprising or consisting essentially of a BRS-3 agonist and a DPP-IV inhibitor for the manufacture of a medicament for reducing body mass. In certain embodiments, the present invention relates to a dosage form of the medicament wherein the BRS-3 agonist and the DPP-IV inhibitor are in amounts sufficient to increase a blood GLP-1 level in a subject.

The present invention additionally features use of a composition comprising or consisting essentially of a BRS-3 agonist and a DPP-IV inhibitor for the manufacture of a medicament for the treatment or prevention of obesity or a condition related thereto. In certain embodiments, the present invention relates to a dosage form of the medicament wherein the BRS-3 agonist and the DPP-IV inhibitor are in amounts sufficient to increase a blood GLP-1 level in a subject.

The present invention additionally features use of a composition comprising or consisting essentially of a BRS-3 agonist and a DPP-IV inhibitor for the manufacture of a medicament for the treatment or prevention of a condition ameliorated by increasing a blood GLP-1 level. In certain embodiments, the present invention relates to a dosage form of the medicament wherein the BRS-3 agonist and the DPP-IV inhibitor are in amounts sufficient to increase a blood GLP-1 level in a subject.

The present invention additionally features use of a composition comprising or consisting essentially of a BRS-3 agonist and a DPP-IV inhibitor for the manufacture of a medicament for the treatment or prevention of a deficiency of GLP-1. In certain embodiments, the present invention relates to a dosage form of the medicament wherein the BRS-3 agonist and the DPP-IV inhibitor are in amounts sufficient to increase a blood GLP-1 level in a subject.

In certain embodiments, the subject is a human.

In an eighth aspect, the invention features a method for identifying GLP-1 secretagogues or compounds useful for reducing body mass or compounds useful for treating or preventing a condition ameliorated by increasing a blood GLP-1 level, comprising the steps of:
  (a) contacting a test compound with a host cell or with membrane of a host cell that expresses a G protein-coupled receptor, wherein the G protein-coupled receptor comprises an amino acid sequence selected from the group consisting of:
    (i) amino acids 1-335 of SEQ ID NO:2;
    (ii) amino acids 1-399 of SEQ ID NO:2;
    (iii) amino acids 2-335 of SEQ ID NO:2;
    (iv) amino acids 2-399 of SEQ ID NO:2;
    (v) amino acids 2-335 of SEQ ID NO:2, with the proviso that the receptor does not comprise the methionine residue at amino acid position 1 of SEQ ID NO:2;
    (vi) amino acids 2-399 of SEQ ID NO:2, with the proviso that the receptor does not comprise the methionine residue at amino acid position 1 of SEQ ID NO:2;
    (vii) the amino acid sequence of a G protein-coupled receptor encoded by a polynucleotide comprising a nucleotide sequence, said nucleotide sequence being the sequence obtainable by a process comprising performing polymerase chain reaction (PCR) on a human DNA sample using specific primers SEQ ID NO:3 and SEQ ID NO:4;
    (viii) the amino acid sequence of a G protein-coupled receptor encoded by a polynucleotide comprising a nucleotide sequence, said nucleotide sequence hybridizing under stringent conditions to the complement of SEQ ID NO:1; and
    (ix) a biologically active fragment of any one of (i) to (viii); and
  (b) determining the ability of the test compound to stimulate functionality of the receptor;
wherein the ability of the test compound to stimulate functionality of the receptor is indicative of the test compound being a GLP-1 secretagogue or a compound useful for reducing body mass or a compound useful for preventing or treating a condition ameliorated by increasing a blood GLP-1 level.

In certain embodiments, the method is a method for identifying GLP-1 secretagogues.

In certain embodiments, the method is a method for identifying compounds useful for reducing body mass.

In certain embodiments, the method is a method for identifying compounds useful for treating or preventing a condition ameliorated by increasing a blood GLP-1 level.

The invention additionally features a method for identifying GLP-1 secretagogues or compounds useful for reducing body mass or compounds useful for treating or preventing a condition ameliorated by increasing a blood GLP-1 level, comprising steps (a) and (b) of this eighth aspect, and further comprising:
  (c) contacting a compound which stimulates functionality of the receptor in step (b) in vitro with a mammalian enteroendocrine cell; and
  (d) determining whether the compound stimulates GLP-1 secretion from the mammalian enteroendocrine cell;
wherein the ability of the test compound to stimulate GLP-1 secretion from the mammalian enteroendocrine cell is indicative of the test compound being a GLP-1 secretagogue or a compound useful for reducing body mass or a compound useful for treating or preventing a condition ameliorated by increasing a blood GLP-1 level. In certain embodiments, the mammalian enteroendocrine cell is GLUTag enteroendocrine L-cell line.

The invention additionally features a method for identifying GLP-1 secretagogues or compounds useful for reducing body mass or compounds useful for treating or preventing a condition ameliorated by increasing a blood GLP-1 level, comprising steps (a) and (b) of this eighth aspect, and further comprising:
  (c) administering a compound which stimulates functionality of the receptor in step (b) to a mammal; and
  (d) determining whether the compound increases a blood GLP-1 level in the mammal;
wherein the ability of the test compound to increase a blood GLP-1 level in the mammal is indicative of the test compound being a GLP-1 secretagogue or a compound useful for reducing body mass or a compound useful for treating or preventing a condition ameliorated by increasing a blood GLP-1 level. In certain embodiments, the mammal is a non-human mammal.

In certain embodiments, the identified GLP-1 secretagogue or the identified compound useful for reducing body mass or the identified compound useful for treating or preventing a condition ameliorated by increasing a blood GLP-1 level is an agonist of the receptor. In some embodiments, the agonist is a partial agonist.

In certain embodiments, receptor is coupled to a G protein. In certain embodiments, the G protein is Gq.

In certain embodiments, the process is RT-PCR (reverse transcription-polymerase chain reaction). RT-PCR techniques are well known to the skilled artisan.

In certain embodiments, the human DNA sample is human cDNA. In certain embodiments, the cDNA is from a human tissue that expresses BRS-3. In some embodiments, the human tissue that expresses BRS-3 is hypothalamus or uterus.

In certain embodiments, stringent hybridization conditions comprise hybridization at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing at 65° C. in a solution comprising 0.1×SSC. Hybridization techniques are well known to the skilled artisan.

In certain embodiments, the G protein-coupled receptor encoded by a polynucleotide comprising a nucleotide sequence, said nucleotide sequence hybridizing under stringent conditions to the complement of SEQ ID NO:1, exhibits a biological activity selected from the group consisting of increasing a level of intracellular IP3 and binding a known ligand of BRS-3. In certain embodiments, the encoded G protein-coupled receptor increases a level of intracellular IP3 and binds a known ligand of BRS-3.

In some embodiments, the G protein-coupled receptor is part of a fusion protein comprising a G protein. Techniques for making a GPCR:G fusion construct are well known to the skilled artisan (see, e.g., International Application WO 02/42461).

In some embodiments, the G protein-coupled receptor is recombinant.

In certain embodiments, the host cell comprises an expression vector, said expression vector comprising a polynucleotide encoding the G protein-coupled receptor. In some embodiments, the expression vector is pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. Other suitable expression vectors will be readily apparent to those of ordinary skill in the art, and a wide variety of expression vectors are commercially available (e.g., from Clontech, Palo Alto, Calif.; Stratagene, La Jolla, Calif.; and Invitrogen, Carlsbad, Calif.).

Suitable host cells of the invention include any eukaryotic cell capable of expressing a G protein-coupled receptor of the invention. The eukaryotic cell can be an animal cell (e.g., an insect, mammal, fish, amphibian, bird or reptile cell), a plant cell (for example a maize or *Arabidopsis* cell), or a fungal cell (for example a *S. cerevisiae* cell). In some embodiments, the host cell is mammalian. Exemplary mammalian host cells include but are not limited to: monkey kidney cells (COS cells), monkey kidney CVI cells transformed by SV40 (COS-7, ATCC CRL 1651); human embryonic kidney cells (HEK-293 ["293"], Graham et al. J. Gen Virol. 36:59 (1977)); human embryonic kidney cells (HEK-293T ["293T"], originally referred to as 293tsA1609neo, DuBridge et al. Mol Cell Biol 7:379-387 (1987)); baby hamster kidney cells (BHK, ATCC CCL 10); chinese hamster ovary-cells (CHO, Urlaub and Chasin, Proc. Natl. Acad. Sci. (USA) 77:4216, (1980); Syrian golden hamster cells MCB3901 (ATCC CRL-9595); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N. Y. Acad. Sci 383:44-68 (1982)); NIH/3T3 cells (ATCC CRL-1658); and mouse L cells (ATCC CCL-1). In some embodiments, the mammalian host cell is selected from the group consisting of 293, 293T, CHO, MCB3901, and COS-7. In certain embodiments, melanophore cells are used. In some embodiments, the host cell is an insect cell (for example a *Spodoptera frugiperda* insect Sf9 cell (ATCC CRL-1711)). In some embodiments, the host cell is a fungal cell (for example a *S. cerevisiae* cell). In some embodiments, the host cell is an enteroendocrine cell. In some embodiments, the enteroendocrine cell is GLUTag enteroendocrine L-cell line. Other suitable host cells will be readily apparent to those of ordinary skill in the art, and a wide variety of cell lines are available from the American Type Culture Collection, 10801 University Boulevard, Manassas, Va. 20110-2209.

In certain embodiments, said determining is consistent with the G protein-coupled receptor being coupled to Gq.

In some embodiments, said determining is consistent with the G protein-coupled receptor being coupled through a promiscuous G protein, such as Gα15 or Gα16, to the phospholipase C pathway. Promiscuous G proteins are well known to the skilled artisan [see, e.g., Offermanns et al., J Biol Chem (1995) 270:15175-15180]. In some embodiments, said determining is consistent with the G protein-coupled receptor being coupled through a chimeric G protein, e.g. to the phospholipase C pathway. Chimeric G proteins are well known to the skilled artisan [see, e.g., Milligan et al., Trends in Pharmaceutical Sciences (1999) 20:118-124; and WO 02/42461].

In some embodiments, said determining is through the measurement of a level of a second messenger.

In some embodiments, said determining is through the measurement of a level of a second messenger selected from the group consisting of cyclic AMP (cAMP), cyclic GMP (cGMP), inositol 1,4,5-triphosphate (IP3), diacylglycerol (DAG), MAP kinase activity, MAPK/ERK kinase kinase-1 (MEKK1) activity, and Ca2+. In some preferred embodiments, the second messenger is IP3. In certain preferred embodiments, a level of intracellular IP3 is increased. In some preferred embodiments, the second messenger is Ca2+. In certain preferred embodiments, a level of intracellular Ca2+ is increased. In some embodiments, said Ca2+ measurement is carried out by FLIPR.

In certain embodiments, said determining is carried out with membrane comprising the G protein-coupled receptor.

In certain embodiments, said determining is through the use of a melanophore assay. In some preferred embodiments, a level of pigment dispersion is increased.

In some embodiments, said determining is through the measurement of an activity mediated by elevation of a level of intracellular IP3. In some embodiments, said activity is stimulation of GLP-1 secretion.

In some embodiments, said determining is through AP1-reporter assay. In some embodiments, said determining is through SRF-reporter assay. In some embodiments, said reporter is luciferase. In some embodiments, said reporter is β-galactosidase. In certain embodiments, a level of luciferase activity or β-galactosidase activity is increased.

In some embodiments, said determining is through the measurement of GTPγS binding to membrane comprising the G protein-coupled receptor. In some preferred embodiments, said GTPγS is labeled with [$^{35}$S]. In some preferred embodiments, said GTPγS binding to membrane comprising the GPCR is increased.

In some embodiments, the candidate compound is a small molecule. In some embodiments, the candidate compound is a small molecule, with the proviso that the small molecule is not a polypeptide. In some embodiments, the candidate compound is a small molecule, with the proviso that the small molecule is not an antibody or an antigen-binding fragment thereof. In some embodiments, the candidate compound is a small molecule, with the proviso that the small molecule is not a lipid. In some embodiments, the candidate compound is a small molecule, with the proviso that the small molecule is not a polypeptide or a lipid. In some embodiments, the candidate compound is a polypeptide. In some embodiments, the candidate compound is a polypeptide, with the proviso that the polypeptide is not an antibody or an antigen-binding fragment thereof. In some embodiments, the candidate compound is a lipid. In some embodiments, the candidate compound is not an antibody or an antigen-binding fragment thereof. In some embodiments, the candidate compound is an antibody or an antigen-binding fragment thereof.

In some embodiments, the method further comprises synthesizing the GLP-1 secretagogue or the compound useful for treating or preventing a condition ameliorated by increasing a blood GLP-1 level.

In some embodiments, the method further comprises: optionally, determining the structure of the GLP-1 secretagogue or the compound useful for reducing body mass or the compound useful for treating or preventing a condition ameliorated by increasing a blood GLP-1 level; and providing the GLP-1 secretagogue or the compound useful for reducing body mass or the compound useful for treating or preventing a condition ameliorated by increasing a blood GLP-1 level or providing the name or structure of the GLP-1 secretagogue or the compound useful for reducing body mass or the compound useful for treating or preventing a condition ameliorated by increasing a blood GLP-1 level.

In some embodiments, said method further comprises: optionally, determining the structure of the GLP-1 secretagogue or the compound useful for reducing body mass or the compound useful for treating or preventing a condition ameliorated by increasing a blood GLP-1 level; optionally, providing the name or structure of the GLP-1 secretagogue or the compound useful for reducing body mass or the compound useful for treating or preventing a condition ameliorated by increasing a blood GLP-1 level; and producing or synthesizing the GLP-1 secretagogue or the compound useful for reducing body mass or the compound useful for treating or preventing a condition ameliorated by increasing a blood GLP-1 level.

In a ninth aspect, the invention features a method for identifying GLP-1 secretagogues or compounds useful for reducing body mass or compounds useful for treating or preventing a condition ameliorated by increasing a blood GLP-1 level, comprising the steps of:
  (a) contacting a G protein-coupled receptor with an optionally labeled known ligand to the receptor in the presence or absence of a test compound, wherein the G protein-coupled receptor comprises an amino acid sequence selected from the group consisting of:
    (i) amino acids 1-335 of SEQ ID NO:2;
    (ii) amino acids 1-399 of SEQ ID NO:2;
    (iii) amino acids 2-335 of SEQ ID NO:2;
    (iv) amino acids 2-399 of SEQ ID NO:2;
    (v) amino acids 2-335 of SEQ ID NO:2, with the proviso that the receptor does not comprise the methionine residue at amino acid position 1 of SEQ ID NO:2;
    (vi) amino acids 2-399 of SEQ ID NO:2, with the proviso that the receptor does not comprise the methionine residue at amino acid position 1 of SEQ ID NO:2;
    (vii) the amino acid sequence of a G protein-coupled receptor encoded by a polynucleotide comprising a nucleotide sequence, said nucleotide sequence being the sequence obtainable by a process comprising performing polymerase chain reaction (PCR) on a human DNA sample using specific primers SEQ ID NO:3 and SEQ ID NO:4;
    (viii) the amino acid sequence of a G protein-coupled receptor encoded by a polynucleotide comprising a nucleotide sequence, said nucleotide sequence hybridizing under stringent conditions to the complement of SEQ ID NO:1; and
    (ix) a biologically active fragment of any one of (i) to (viii); and
  (b) detecting the complex between said known ligand and said receptor; and
  (c) determining whether less of said complex is formed in the presence of the test compound than in the absence of the test compound;
wherein said determination is indicative of the test compound being a GLP-1 secretagogue or a compound useful for reducing body mass or a compound useful for preventing or treating a condition ameliorated by increasing a blood GLP-1 level.

In certain embodiments, the method is a method for identifying GLP-1 secretagogues.

In certain embodiments, the method is a method for identifying compounds useful for reducing body mass.

In certain embodiments, the method is a method for identifying compounds useful for treating or preventing a condition ameliorated by increasing a blood GLP-1 level.

In certain embodiments, the known ligand is selected from the group consisting of Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, Compound 26, Compound 27, Compound 28, Compound 29, Compound 30, Compound 31, Compound 32, Compound 33, and Compound 34.

In certain embodiments, the optionally labeled known ligand is a labeled known ligand. In certain embodiments, the labeled known ligand is a radiolabeled known ligand. Techniques for radiolabeling a compound, such as for labeling a known ligand of a G protein-coupled receptor of the invention, are well known to the skilled artisan. See, e.g., International Application WO 04/065380.

Techniques for detecting the complex between a G protein-coupled receptor and a compound known to be a ligand of the G protein-coupled receptor are well known to the skilled artisan. See, e.g., International Application WO 04/065380.

The invention additionally features a method for identifying GLP-1 secretagogues or compounds useful for reducing body mass or compounds useful for treating or preventing a condition ameliorated by increasing a blood GLP-1 level, comprising steps (a) to (c) of this ninth aspect, and further comprising:
  (d) contacting a compound in the presence of which less of said complex is formed in step (c) in vitro with a mammalian enteroendocrine cell; and
  (e) determining whether the compound stimulates GLP-1 secretion from the mammalian enteroendocrine cell;
wherein the ability of the test compound to stimulate GLP-1 secretion from the mammalian enteroendocrine cell is indicative of the test compound being a GLP-1 secretagogue or a compound useful for reducing body mass or a compound useful for treating or preventing a condition ameliorated by increasing a blood GLP-1 level. In certain embodiments, the mammalian enteroendocrine cell is GLUTag enteroendocrine L-cell line.

The invention additionally features a method for identifying GLP-1 secretagogues or compounds useful for reducing body mass or compounds useful for treating or preventing a condition ameliorated by increasing a blood GLP-1 level, comprising steps (a) to (c) of this ninth aspect, and further comprising:
  (d) administering a compound in the presence of which less of said complex is formed in step (c) to a mammal; and (e) determining whether the compound increases a blood GLP-1 level in the mammal;

wherein the ability of the test compound to increase a blood GLP-1 level in the mammal is indicative of the test compound being a GLP-1 secretagogue or a compound useful for reducing body mass or a compound useful for treating or preventing a condition ameliorated by increasing a blood GLP-1 level. In certain embodiments, the mammal is a non-human mammal.

In certain embodiments, the receptor is recombinant.

This application claims the benefit of priority from the following provisional application, filed via U.S. Express mail with the United States Patent and Trademark Office on the indicated date: U.S. Provisional No. 60/675,730, filed Apr. 27, 2005. The disclosure of the foregoing application is herein incorporated by reference in its entirety.

BRIEF DESCRIPTION OF THE DRAWINGS

The invention is illustrated in connection with the figures appended hereto in which:

FIG. 1 shows increase in intracellular IP3 accumulation by BRS-3. See Example 9.

FIG. 2 shows expression of BRS-3 in GLUTag cells. See Example 10.

DETAILED DESCRIPTION OF THE INVENTION

The present invention is concerned with the combination of certain compounds, or pharmaceutically acceptable salts thereof, for the treatment or prevention of diabetes and conditions related thereto. The present invention is additionally concerned with the combination of certain compounds, or pharmaceutically acceptable salts thereof, for reducing body mass. The present invention is additionally concerned with the combination of certain compounds, or pharmaceutically acceptable salts thereof, for the treatment or prevention of obesity and conditions related thereto. The present invention is additionally concerned with the combination of certain compounds, or pharmaceutically acceptable salts thereof, for the treatment or prevention of a condition ameliorated by increasing a blood GLP-1 level. The present invention is additionally concerned with methods of using a G protein-coupled receptor of the invention to screen test compounds as GLP-1 secretagogues. Applicant has discovered that BRS-3 is expressed by mammalian GLP-1 producing enteroendocrine L-cell. BRS-3 is a GLP-1 secretagogue receptor. Agonists of BRS-3 are GLP-1 secretagogues.

By the use of a combination of a BRS-3 agonist and a DPP-IV inhibitor in accordance with the present invention, it is possible to treat or prevent diabetes and conditions related thereto with a dose of a DPP-IV inhibitor substantially lower than that currently contemplated for use in therapy for diabetes and conditions related thereto, thereby reducing the likelihood of unwanted side-effects associated with inhibition of DPP-IV activity. By the use of a combination of a BRS-3 agonist and a DPP-IV inhibitor in accordance with the present invention, it is possible to reduce body mass with a dose of a DPP-IV inhibitor substantially lower than that currently contemplated for reducing body mass, thereby reducing the likelihood of unwanted side-effects associated with inhibition of DPP-IV activity. By the use of a combination of a BRS-3 agonist and a DPP-IV inhibitor in accordance with the present invention, it is possible to treat or prevent obesity and conditions related thereto with a dose of a DPP-IV inhibitor substantially lower than that currently contemplated for use in therapy for obesity and conditions related thereto, thereby reducing the likelihood of unwanted side-effects associated with inhibition of DPP-IV activity. By the use of a combination of a BRS-3 agonist and a DPP-IV inhibitor in accordance with the present invention, it is possible to treat or prevent a condition ameliorated by increasing a blood GLP-1 level with a dose of a DPP-IV inhibitor substantially lower than that currently contemplated for use in therapy for said condition, thereby reducing the likelihood of unwanted side-effects associated with inhibition of DPP-IV activity. Furthermore, by the use of a combination of a BRS-3 agonist and a DPP-IV inhibitor in accordance with the present invention, it is possible to treat or prevent diabetes or obesity and conditions related thereto with a dose of a BRS-3 agonist substantially lower than that currently contemplated for use in therapy for diabetes or obesity and conditions related thereto, thereby reducing the likelihood of unwanted side-effects should any be found to be associated with activation of BRS-3 receptor. The present invention provides a new, unexpected and advantageous approach to lowering a blood glucose level in a subject. The present invention additionally provides a new, unexpected and advantageous approach to increasing a blood GLP-1 level in a subject. The present invention additionally provides a new, unexpected and advantageous approach to screening a test compound as a GLP-1 secretagogue.

The term "ligand", as used herein, shall mean a molecule that specifically binds to a GPCR. A ligand may be, for example, a polypeptide, a lipid, a small molecule, an antibody. An endogenous ligand is a ligand that is an endogenous, natural ligand for a native GPCR. A ligand may be a GPCR "antagonist", "agonist", "partial agonist", or "inverse agonist", or the like.

The term "agonist", as used herein, shall mean an agent (e.g., ligand, candidate compound) that by virtue of binding to a GPCR activates the GPCR so as to elicit an intracellular response mediated by the GPCR.

The term "partial agonist", as used herein, shall mean an agent (e.g., ligand, candidate compound) that by virtue of binding to a GPCR activates the GPCR so as to elicit an intracellular response mediated by the GPCR, albeit to a lesser extent or degree than does a full agonist.

The term "antagonist" shall mean an agent (e.g., ligand, candidate compound) that binds, and preferably binds competitively, to a GPCR at about the same site as an agonist or partial agonist but which does not activate an intracellular response initiated by the active form of the GPCR, and can thereby inhibit the intracellular response by agonist or partial agonist. An antagonist typically does not diminish the baseline intracellular response in the absence of an agonist or partial agonist.

The term "inverse agonist" shall mean an agent (e.g., ligand, candidate compound) which binds to a GPCR and which inhibits the baseline intracellular response initiated by the active form of the receptor below the normal base level activity which is observed in the absence of an agonist or partial agonist.

The term "BRS-3 agonist," as used herein, refers to a compound that binds to BRS-3 receptor and acts as an agonist.

The term "selective BRS-3 agonist," as used herein, refers to a BRS-3 agonist having selectivity for BRS-3 receptor over one or more closely related receptors, such as gastric-releasing peptide receptor (GRP-R) or neuromedin B receptor (NMB-R).

The term "DPP-IV inhibitor," as used herein, refers to a compound that binds to DPP-IV and inhibits DPP-IV dipeptidyl peptidase activity.

The term "selective DPP-IV inhibitor," as used herein, refers to a DPP-IV inhibitor having selectivity for DPP-IV over closely related peptidases, such as one or more of post-proline-cleaving enzyme (PPCE), dipeptidyl peptidase II (DPP-II), dipeptidyl peptidase 8 (DPP-8), and dipeptidyl peptidase 9 (DPP-9).

The term "blood glucose level" or "blood GLP-1 level" shall mean blood glucose concentration or blood GLP-1 concentration, respectively. In certain embodiments, blood GLP-1 level is a level in blood of biologically active GLP-1, wherein GLP-1 having agonist activity at GLP-1R is biologically active. In certain embodiments, a blood glucose level or blood GLP-1 level is a plasma glucose level or a plasma GLP-1 level.

The term "elevated blood glucose level" shall mean an elevated blood glucose level such as that found in a subject demonstrating clinically inappropriate basal and postprandial hyperglycemia or such as that found in a subject in oral glucose tolerance test (oGTT).

The term "subject," as used herein, shall refer to a mammal, including but not limited to a mouse, a rat, a rabbit, a pig, a dog, a cat, a non-human primate and a human, more preferably to a mouse or rat, most preferably to a human.

The term "in need of prevention or treatment" as used herein refers to a judgement made by a caregiver (e.g. physician, nurse, nurse practitioner in the case of humans; veterinarian in the case of non-human mammals) that a subject requires or will benefit from treatment.

The term "therapeutically effective amount" or "therapeutically effective dose" is intended to mean that amount of drug that will elicit the desired biological or medical response. In certain embodiments, a therapeutically effective amount is that amount of drug which will create an AUC inhibition above 30% in mouse oGTT assay.

The term "therapeutically ineffective amount" or "therapeutically ineffective dose" is intended to mean an amount of drug less than the therapeutically effective amount of the drug. In certain embodiments, a therapeutically ineffective amount is an amount of drug which will create an AUC inhibition less than or equal to 30% in mouse oGTT assay.

The term "amount that is effective to prevent" refers to that amount of drug that will prevent or reduce the risk of occurrence of the biological or medical event that is sought to be prevented. In many instances, the amount that is effective to prevent is the same as the therapeutically effective amount.

The term "composition" shall mean a material comprising at least one component.

The term "active ingredient" shall mean any component that provides pharmacological activity or other direct effect in the diagnosis, cure, mitigation, treatment, or prevention of disease.

The term "pharmaceutical composition" shall mean a composition comprising at least one active ingredient, whereby the composition is amenable to investigation for a specified, efficacious outcome in a mammal.

The term "dosage form" shall mean the physical form in which a drug is produced and dispensed, such as a tablet, capsule, or an injectable.

The term "obesity," as used herein, is defined as a body-mass index (BMI) of 30.0 or greater, in accordance with the WHO classifications of weight [Kopelman, Nature (2000) 404:635-643; the disclosure of which is herein incorporated by reference in its entirety].

The term "condition related to obesity" is intended to include but not be limited to hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, Type 2 diabetes, dyslipidemia, hyperandrogenemia in women, polycystic ovarian syndrome, dysmenorrhea, infertility, pregnancy complications, and male hypogonadism, where it is understood that conditions related to obesity can be included in embodiments individually or in any combination.

The term "overweight," as used herein, is defined as a body mass index (BMI) of 27-29.9.

As used herein, the term "diabetes" encompasses both insulin-dependent diabetes mellitus (also known as Type 1 diabetes) and non-insulin-dependent diabetes mellitus (also known as Type 2 diabetes).

The term "condition related to diabetes" is intended to include but not be limited to hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity, where it is understood that conditions related to diabetes can be included in embodiments individually or in any combination.

The term "condition ameliorated by increasing a blood GLP-1 level" is intended to include but not be limited to diabetes, a condition related to diabetes, myocardial infarction, learning impairment, memory impairment, and a neurodegenerative disorder, where it is understood that conditions ameliorated by increasing a blood GLP-1 level can be included in embodiments individually or in any combination.

The term "atherosclerosis" as used herein refers to a form of vascular disease characterized by the deposition of atheromatous plaques containing cholesterol and lipids on the innermost layer of the walls of large and medium-sized arteries.

The term "metabolic syndrome" as defined herein, and according to the Adult Treatment Panel III (ATP III; National Institutes of Health: Third Report of the National Cholesterol Education Program Expert Panel on Detection, Evaluation, and Treatment of High Blood Cholesterol in Adults (Adult Treatment Panel III), Executive Summary; Bethesda, Md., National Institutes of Health, National Heart, Lung and Blood Institute, 2001 (NIH pub. No 01-3670), occurs when a person meets three or more of five criteria related to obesity, hypertriglyceridemia, low HDL cholesterol, high blood pressure, and high fasting glucose.

The term "neurodegenerative disorder" is intended to include but not be limited to excitotoxic brain damage caused by severe epileptic seizures, Alzheimer's disease, Parkinson's disease, Huntington's disease, prion-associated disease, stroke, motor-neuron disease, learning or memory impairment, traumatic brain injury, spinal cord injury, and peripheral neuropathy.

Chemical Group, Moiety or Radical

The term "$C_{1-5}$ acyl" denotes a $C_{1-5}$ alkyl radical attached to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl and the like.

The term "$C_{1-5}$ acyloxy" denotes an acyl radical attached to an oxygen atom wherein acyl has the same definition has described herein; some examples include but not limited to acetyloxy, propionyloxy, butanoyloxy, iso-butanoyloxy, sec-butanoyloxy, t-butanoyloxy and the like.

The term "$C_{1-6}$ acylsulfonamide" refers to a $C_{1-6}$ acyl attached directly to the nitrogen of the sulfonamide, wherein the definitions for $C_{1-6}$ acyl and sulfonamide have the same meaning as described herein, and a $C_{1-6}$ acylsulfonamide can be represented by the following formula:

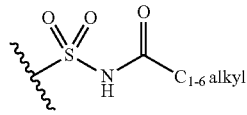

Some embodiments of the present invention are when acylsulfonamide is a $C_{1-5}$ acylsulfonamide, some embodiments are $C_{1-4}$ acylsulfonamide, some embodiments are $C_{1-3}$ acylsulfonamide, and some embodiments are $C_{1-2}$ acylsulfonamide. Examples of an acylsulfonamide include, but not limited to, acetylsulfamoyl [—S(=O)$_2$NHC(=O)Me], propionylsulfamoyl [—S(=O)$_2$NHC(=O)Et], isobutyrylsulfamoyl, butyrylsulfamoyl, 2-methyl-butyrylsulfamoyl, 3-methyl-butyrylsulfamoyl, 2,2-dimethyl-propionylsulfamoyl, pentanoylsulfamoyl, 2-methyl-pentanoylsulfamoyl, 3-methyl-pentanoylsulfamoyl, 4-methyl-pentanoylsulfamoyl, and the like.

The term "$C_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "$C_{1-4}$ alkoxy" as used herein denotes a radical alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "$C_{1-8}$ alkyl" denotes a straight or branched carbon radical containing 1 to 8 carbons, some embodiments are 1 to 6 carbons, some embodiments are 1 to 3 carbons, and some embodiments are 1 or 2 carbons. Examples of an alkyl include, but not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_{1-4}$ alkylcarboxamido" or "$C_{1-4}$ alkylcarboxamide" denotes a single $C_{1-4}$ alkyl group attached to the nitrogen of an amide group, wherein alkyl has the same definition as found herein. The $C_{1-5}$ alkylcarboxamido may be represented by the following:

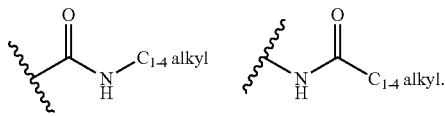

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-3}$ alkylene" refers to a $C_{1-3}$ divalent straight carbon group. In some embodiments $C_{1-3}$ alkylene refers to, for example, —CH$_2$—, —CH$_2$CH$_2$—, —CH$_2$CH$_2$CH$_2$—, and the like. In some embodiments, $C_{1-3}$ alkylene refers to —CH—, —CHCH$_2$—, —CHCH$_2$CH$_2$—, and the like wherein these examples relate generally to "A".

The term "$C_{1-4}$ alkylsulfinyl" denotes a $C_{1-4}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-4}$ alkylsulfonamide" refers to the groups

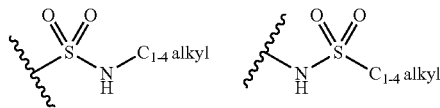

wherein $C_{1-4}$ alkyl has the same definition as described herein.

The term "$C_{1-4}$ alkylsulfonyl" denotes a $C_{1-4}$ alkyl radical attached to a sulfone radical of the formula: —S(O)$_2$— wherein the alkyl radical has the same definition as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butyl, and the like.

The term "$C_{1-4}$ alkylthio" denotes a $C_{1-4}$ alkyl radical attached to a sulfide of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{1-4}$ alkylthiocarboxamide" denotes a thioamide of the following formulae:

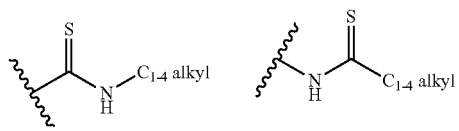

wherein $C_{1-4}$ alkyl has the same definition as described herein.

The term "$C_{1-4}$ alkylthioureyl" denotes the group of the formula: —NC(S)N— wherein one are both of the nitrogens are substituted with the same or different $C_{1-4}$ alkyl groups and alkyl has the same definition as described herein. Examples of an alkylthioureyl include, but not limited to, CH$_3$NHC(S)NH—, NH$_2$C(S)NCH$_3$—, (CH$_3$)$_2$N(S)NH—, (CH$_3$)$_2$N(S)NH—, (CH$_3$)$_2$N(S)NCH$_3$—, CH$_3$CH$_2$NHC(S)NH—, CH$_3$CH$_2$NHC(S)NCH$_3$—, and the like.

The term "$C_{1-4}$ alkylureyl" denotes the group of the formula: —NC(O)N— wherein one are both of the nitrogens substituted with the same or different $C_{1-4}$ alkyl group wherein alkyl has the same definition as described herein.

Examples of an alkylureyl include, but not limited to, CH₃NHC(O)NH—, NH₂C(O)NCH₃—, (CH₃)₂N(O)NH—, (CH₃)₂N(O)NH—, (CH₃)₂N(O)NCH₃—, CH₃CH₂NHC(O)NH—, CH₃CH₂NHC(O)NCH₃—, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include, but not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "amino" denotes the group —NH₂.

The term "$C_{1-4}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylalkyl" defines a $C_1$-$C_4$ alkylene, such as —CH₂—, —CH₂CH₂— and the like, which is further substituted with an aryl group. Examples of an "arylalkyl" include benzyl, phenethylene and the like.

The term "arylcarboxamido" denotes a single aryl group attached to the nitrogen of an amide group, wherein aryl has the same definition as found herein. The example is N-phenylcarboxamide.

The term "arylureyl" denotes the group —NC(O)N— where one of the nitrogens are substituted with an aryl.

The term "benzyl" denotes the group —CH₂C₆H₅.

The term "carbo-$C_{1-6}$-alkoxy" refers to a $C_{1-6}$ alkyl ester of a carboxylic acid, wherein the alkyl group is as defined herein. In some embodiments, the carbo-$C_{1-6}$-alkoxy group is bonded to a nitrogen atom and together form a carbamate group (e.g., N—COO—$C_{1-6}$-alkyl). In some embodiments, the carbo-$C_{1-6}$-alkoxy group is an ester (e.g., —COO—$C_{1-6}$-alkyl). Examples include, but not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neopentoxy, carbo-n-hexyloxy, and the like.

The term "carboxamide" refers to the group —CONH₂.

The term "carboxy" or "carboxyl" denotes the group —CO₂H; also referred to as a carboxylic acid group.

The term "cyano" denotes the group —CN.

The term "$C_{3-7}$ cycloalkenyl" denotes a non-aromatic ring radical containing 3 to 6 ring carbons and at least one double bond; some embodiments contain 3 to 5 carbons; some embodiments contain 3 to 4 carbons. Examples include cyclopropenyl, cyclobutenyl, cyclopentenyl, cyclopentenyl, cyclohexenyl, and the like.

The term "$C_{3-7}$ cycloalkyl" denotes a saturated ring radical containing 3 to 6 carbons; some embodiments contain 3 to 5 carbons; some embodiments contain 3 to 4 carbons. Examples include cyclopropyl, cyclobutyl, cyclopentyl, cyclopenyl, cyclohexyl, cycloheptyl and the like.

The term "$C_{4-8}$ diacylamino" denotes an amino group bonded with two acyl groups defined herein wherein the acyl groups may be the same or different, such as:

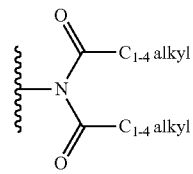

Examples of $C_{4-8}$ diacylamino groups include, but limited to, diacetylamino, dipropionylamino, acetylpropionylamino and the like.

The term "$C_{2-6}$ dialkylamino" denotes an amino substituted with two of the same or different alkyl radicals wherein alkyl radical has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like. Some embodiments are "$C_{2-4}$ dialkylamino."

The term "$C_{1-4}$ dialkylcarboxamido" or "$C_{1-4}$ dialkylcarboxamide" denotes two alkyl radicals, that are the same or different, attached to an amide group, wherein alkyl has the same definition as described herein. A $C_{1-4}$ dialkylcarboxamido may be represented by the following groups:

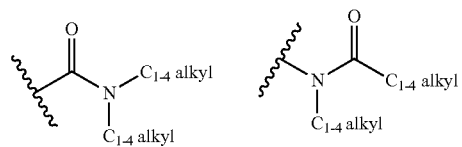

wherein $C_{1-4}$ has the same definition as described herein. Examples of a dialkylcarboxamide include, but not limited to, N,N-dimethylcarboxamide, N-methyl-N-ethylcarboxamide, N,N-diethylcarboxamide, N-methyl-N-isopropylcarboxamide, and the like.

The term "$C_{2-6}$ dialkylsulfonamide" refers to one of the following groups shown below:

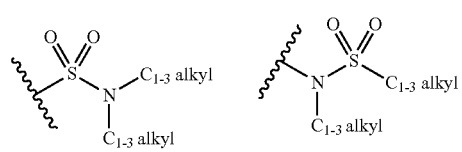

wherein $C_{1-3}$ has the same definition as described herein, for example but not limited to, methyl, ethyl, n-propyl, isopropyl, and the like.

The term "$C_{2-6}$ dialkylthiocarboxamido" or "$C_{2-6}$ dialkylthiocarboxamide" denotes two alkyl radicals, that are the same or different, attached to a thioamide group, wherein alkyl has the same definition as described herein. A $C_{1-4}$ dialkylthiocarboxamido may be represented by the following groups:

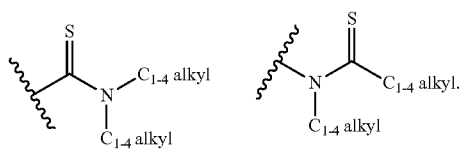

Examples of a dialkylthiocarboxamide include, but not limited to, N,N-dimethylthiocarboxamide, N-methyl-N-ethylthiocarboxamide and the like.

The term "$C_{2-6}$ dialkylsulfonylamino" refers to an amino group bonded with two $C_{1-3}$ alkylsulfonyl groups as defined herein.

The term "ethynylene" refers to the carbon-carbon triple bond group as represented below:

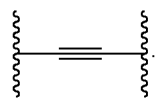

The term "formyl" refers to the group —CHO.

The term "$C_{1-4}$ haloalkoxy" denotes a haloalkyl, as defined herein, which is directly attached to an oxygen atom. Examples include, but not limited to, difluoromethoxy, trifluoromethoxy, 2,2,2-trifluoroethoxy, pentafluoroethoxy and the like.

The term "$C_{1-4}$ haloalkyl" denotes an $C_{1-4}$ alkyl group, defined herein, wherein the alkyl is substituted with one halogen up to fully substituted and a fully substituted $C_{1-4}$haloalkyl can be represented by the formula $C_nL_{2n+1}$ wherein L is a halogen and "n" is 1, 2, 3 or 4; when more than one halogen is present then they may be the same or different and selected from the group consisting of F, Cl, Br and I, preferably F. Examples of $C_{1-4}$ haloalkyl groups include, but not limited to, fluoromethyl, difluoromethyl, trifluoromethyl, chlorodifluoromethyl, 2,2,2-trifluoroethyl, pentafluoroethyl and the like.

The term "$C_{1-4}$ haloalkylcarboxamide" denotes an alkylcarboxamide group, defined herein, wherein the alkyl is substituted with one halogen up to fully substituted represented by the formula $C_nL_{2n+1}$ wherein L is a halogen and "n" is 1, 2, 3 or 4. When more than one halogen is present they may be the same or different and selected from the group consisting of F, Cl, Br and I, preferably F.

The term "$C_{1-4}$ haloalkylsulfinyl" denotes a haloalkyl radical attached to a sulfoxide group of the formula: —S(O)— wherein the haloalkyl radical has the same definition as described herein. Examples include, but not limited to, trifluoromethylsulfinyl, 2,2,2-trifluoroethylsulfinyl, 2,2-difluoroethylsulfinyl and the like.

The term "$C_{1-4}$ haloalkylsulfonyl" denotes a haloalkyl radical attached to a sulfone group of the formula: —S(O)$_2$— wherein haloalkyl has the same definition as described herein. Examples include, but not limited to, trifluoromethylsulfonyl, 2,2,2-trifluoroethylsulfonyl, 2,2-difluoroethylsulfonyl and the like.

The term "$C_{1-4}$ haloalkylthio" denotes a haloalkyl radicaol directly attached to a sulfur wherein the haloalkyl has the same meaning as described herein. Examples include, but not limited to, trifluoromethylthio (i.e., CF$_3$S—), 1,1-difluoroethylthio, 2,2,2-trifluoroethylthio and the like.

The term "halogen" or "halo" denotes to a fluoro, chloro, bromo or iodo group.

The term "$C_{1-2}$ heteroalkylene" refers to a $C_{1-2}$ alkylene bonded to a heteroatom selected from O, S, S(O), S(O)$_2$ and NH. Some represented examples include, but not limited to, the groups of the following formulae:

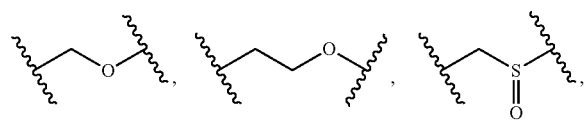

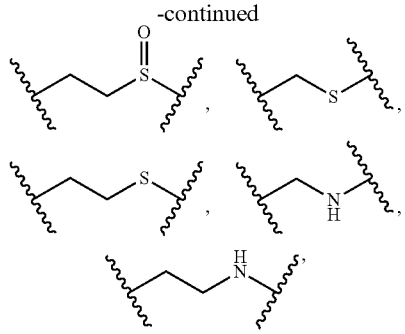

and the like.

The term "heteroaryl" denotes an aromatic ring system that may be a single ring, two fused rings or three fused rings wherein at least one ring carbon is replaced with a heteroatom selected from, but not limited to, the group consisting of O, S and N wherein the N can be optionally substituted with H, $C_{1-4}$ acyl or $C_{1-4}$ alkyl. Examples of heteroaryl groups include, but not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroaryl atom is O, S, NH, examples include, but not limited to, pyrrole, indole, and the like.

The term "heterocyclic" denotes a non-aromatic carbon ring (i.e., cycloalkyl or cycloalkenyl as defined herein) wherein one, two or three ring carbons are replaced by a heteroatom selected from, but not limited to, the group consisting of O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like.

The term "heterocyclic-carbonyl" denotes a heterocyclic group, as defined herein, directly bonded to the carbon of a carbonyl group (i.e., C=O). In some embodiments, a ring nitrogen of the heterocyclic group is bonded to the carbonyl group forming an amide. Examples include, but not limited to,

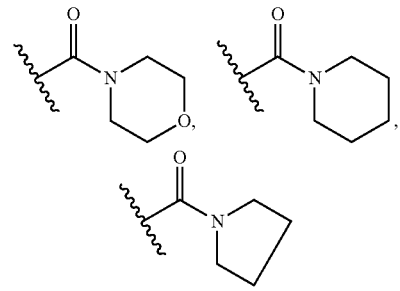

and the like.

In some embodiments, a ring carbon is bonded to the carbonyl group forming a ketone group. Examples include, but not limited to,

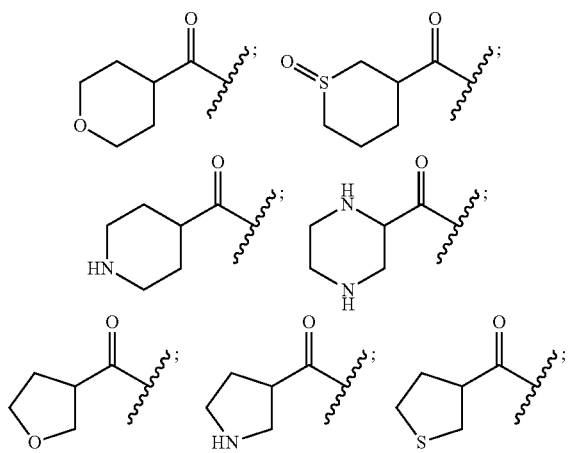

and the like.

The term "heterocyclic-oxy" refers to a heterocyclic group, as defined herein, that is directly bonded to an oxygen atom. Examples include the following:

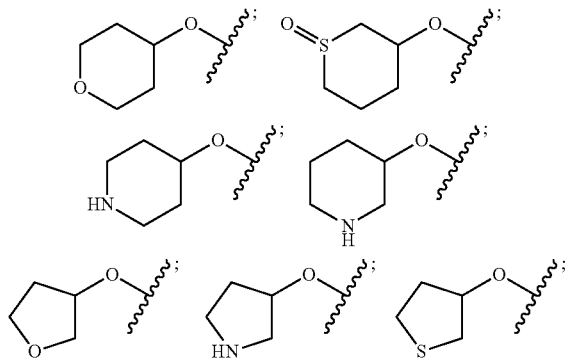

and the like.

The term "heterocycliccarboxamido" denotes a heterocyclic group, as defined herein, with a ring nitrogen where the ring nitrogen is bonded directly to the carbonyl forming an amide. Examples include, but not limited to,

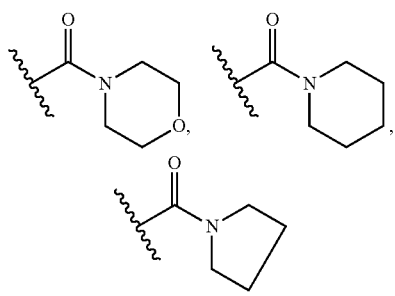

and the like.

The term "heterocyclicsulfonyl" denotes a heterocyclic group, as defined herein, with a ring nitrogen where the ring nitrogen is bonded directly to an $SO_2$ group forming an sulfonamide. Examples include, but not limited to,

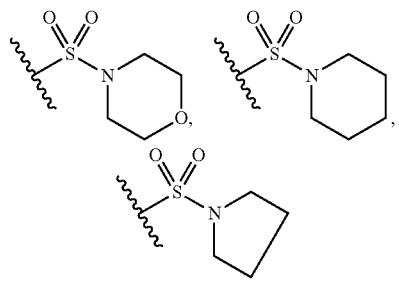

and the like.

The term "hydroxyl" refers to the group —OH.

The term "hydroxylamino" refers to the group —NHOH.

The term "nitro" refers to the group —$NO_2$.

The term "$C_{4-7}$ oxo-cycloalkyl" refers to a $C_{4-7}$ cycloalkyl, as defined herein, wherein one of the ring carbons is replaced with a carbonyl. Examples of $C_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

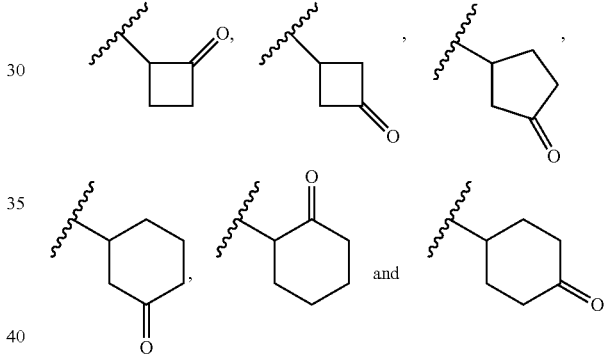

The term "perfluoroalkyl" denotes the group of the formula —$C_nF_{2n+1}$; stated differently, a perfluoroalkyl is an alkyl as defined herein wherein the alkyl is fully substituted with fluorine atoms and is therefore considered a subset of haloalkyl. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

The term "phenoxy" refers to the group $C_6H_5O$—.

The term "phenyl" refers to the group $C_6H_5$—.

The term "phosphonooxy" refers to a group with the following chemical structure:

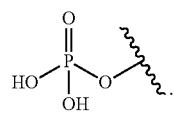

The term "sulfonamide" refers to the group —$SO_2NH_2$.

The term "sulfonic acid" refers to the group —$SO_3H$.

The term "tetrazolyl" refers to the five membered heteroaryl of the following formulae:

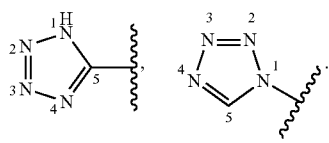 [SMILES: *c1nnn[nH]1 ; *n1cnnn1]

In some embodiments, the tetrazolyl group is further substituted at either the 1 or 5 position respectively with a group selected from the group consisting of $C_{1-3}$ alkyl, $C_{1-3}$ haloalkyl and $C_{1-3}$ alkoxy.

The term "thiol" denotes the group —SH.

The term "Apa" refers to amino-3-phenylpropionic acid.

The term "GLP-1 secretagogue" shall mean an agent (e.g., a compound) that promotes GLP-1 secretion from a cell, e.g. an enteroendocrine cell.

The term "endogenous" shall mean a material that a mammal naturally produces.

The term "biologically active fragment of a G protein-coupled receptor" shall mean a fragment of the GPCR having structural and biochemical functions of a naturally occurring GPCR. In certain embodiments, the biologically active fragment couples to a G protein. In certain embodiments, the biologically active fragment binds to a known ligand of the GPCR.

The term "primer" is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "expression vector" shall mean a DNA sequence that is required for the transcription of cloned DNA and translation of the transcribed mRNA in an appropriate host cell recombinant for the expression vector. An appropriately constructed expression vector should contain an origin of replication for autonomous replication in host cells, selectable markers, a limited number of useful restriction enzyme sites, a potential for high copy number, and active promoters. The cloned DNA to be transcribed is operably linked to a constitutively or conditionally active promoter within the expression vector.

The term "candidate compound" or "test compound" shall mean a compound (for example and not limitation, a chemical compound) that is amenable to screening.

The term "contact" or "contacting" shall mean bringing at least two moieties together.

The terms "modulate" or "modify" shall be taken to refer to an increase or decrease in the amount, quality, or effect of a particular activity, function or molecule. By way of illustration and not limitation, agonists, partial agonists, inverse agonists, and antagonists of a G protein-coupled receptor are modulators of the receptor.

The term "small molecule" shall be taken to mean a compound having a molecular weight of less than about 10,000 grams per mole, including a peptide, peptidomimetic, amino acid, amino acid analogue, polynucleotide, polynucleotide analogue, nucleotide, nucleotide analogue, organic compound or inorganic compound (i.e. including a heteroganic compound or organometallic compound), and salts, esters and other pharmaceutically acceptable forms thereof. In certain preferred embodiments, small molecules are organic or inorganic compounds having a molecular weight of less than about 5,000 grams per mole. In certain preferred embodiments, small molecules are organic or inorganic compounds having molecular weight of less than about 1,000 grams per mole. In certain preferred embodiments, small molecules are organic or inorganic compounds having a molecular weight of less than about 500 grams per mole.

The term "polynucleotide" shall refer to RNA, DNA, or RNA/DNA hybrid sequence of more than one nucleotide in either single chain or duplex form. The polynucleotides of the invention may be prepared by any known method, including synthetic, recombinant, ex vivo generation, or a combination thereof, as well as utilizing any purification methods known in the art.

The term "polypeptide" shall refer to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

The term "antibody" is intended herein to encompass monoclonal antibody and polyclonal antibody.

The term "second messenger" shall mean an intracellular response produced as a result of receptor activation. A second messenger can include, for example, inositol 1,4,5-triphosphate (IP3), diacylglycerol (DAG), cyclic AMP (cAMP), cyclic GMP (cGMP), MAP kinase acitivity, MAPK/ERK kinase kinase-1 (MEKK1) activity, and Ca2+. Second messenger response can be measured for a determination of receptor activation.

The term "receptor functionality" shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins, such as eliciting a second messenger response.

The term "stimulate" or "stimulating," in relationship to the term "response" or "functionality of the receptor" shall mean that a response or a functionality of the receptor is increased in the presence of a compound as opposed to in the absence of the compound.

The term "inhibit" or "inhibiting," in relationship to the term "response" or "functionality of the receptor" shall mean that a response a functionality of the receptor is decreased or prevented in the presence of a compound as opposed to in the absence of the compound.

Where a range of values is provided, it is understood that each intervening value, to the tenth of the lower limit unless the context clearly indicates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

BRS-3 Agonists

Preferably, BRS-3 is mammalian BRS-3. More preferably, BRS-3 is rodent or primate BRS-3. Most preferably, BRS-3 is human BRS-3.

The class of BRS-3 agonists useful in the novel therapeutic combinations of the present invention include compounds which exhibit an acceptably high affinity for BRS-3 receptor. The BRS-3 agonist or pharmaceutically acceptable salt may be any agonist, more preferably a selective BRS-3 agonist.

Examples of BRS-3 agonists are described in Weber et al., J Med Chem (2003) 46:1918-1930, the disclosure of which is herein incorporated by reference in its entirety.

Examples of BRS-3 agonists are described in Mantey et al., J Pharmacol Exp Ther (2004) 310:1161-1169, the disclosure of which is herein incorporated by reference in its entirety.

Examples of BRS-3 agonists are described in Boyle et al., J Peptide Sci (2005) 11:136-141, the disclosure of which is herein incorporated by reference in its entirety.

Examples of BRS-3 agonists are described in Lammerich et al., Br J Pharmacol (2003) 138:1431-1440, the disclosure of which is herein incorporated by reference in its entirety.

In one aspect, the BRS-3 agonist is selected from the left column of Table B.

In one aspect, the BRS-3 agonist is selected from Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, Compound 26, and Compound 27; these Compounds may be found in Boyle et al., J Peptide Sci (2005) 11:136-141, where they are described as selective BRS-3 agonists.

In one aspect, the BRS-3 agonist is selected from Compound 28, Compound 29, and Compound 30; these Compounds may be found in Mantey et al., J Pharmacol Exp Ther (2004) 310:1161-1169, where they are described as selective BRS-3 agonists.

In one aspect, the BRS-3 agonist is selected from Compound 31, Compound 32, and Compound 33; these Compounds may be found in Boyle et al., J Peptide Sci (2005) 11:136-141, where they are described as selective BRS-3 agonists.

In one aspect, the BRS-3 agonist is Compound 34; this Compound may be found in Mantey et al., J Pharmacol Exp Ther (2004) 310:1161-1169, where it is described as non-selective for BRS-3 over GRP-R and NMB-R In one aspect of the present invention, any one or more BRS-3 agonist can be excluded from any embodiment of the present invention.

In one aspect of the present invention, the BRS-3 agonist has an EC50 of less than about 10 µM, less than about 1 µM, less than about 100 nM, less than about 75 nM, less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM. Preferably the BRS-3 agonist has an EC50 of less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM.

In one aspect of the present invention, the BRS-3 agonist is a selective BRS-3 agonist, wherein the selective BRS-3 agonist has a selectivity for BRS-3 over gastric-releasing peptide receptor (GRP-R) or neuromedin B receptor (NMB-R) of at least about 10-fold, more preferably of at least about 100-fold. In one aspect of the present invention, the BRS-3 agonist is a selective BRS-3 agonist, wherein the selective BRS-3 agonist has a selectivity for BRS-3 over gastric-releasing peptide receptor (GRP-R) and neuromedin B receptor (NMB-R) of at least about 10-fold, more preferably of at least about 100-fold.

In one aspect of the present invention, the BRS-3 agonist is orally active.

In one aspect of the present invention, the BRS-3 agonist is an agonist of human BRS-3.

DPP-IV Inhibitors

The class of DPP-IV inhibitors useful in the novel therapeutic combinations of the present invention include compounds which exhibit an acceptably high affinity for DPP-IV. The DPP-IV inhibitor or pharmaceutically acceptable salt may be any DPP-IV inhibitor, more preferably a selective dipeptidyl peptidase inhibitor, and most preferably a selective DPP-IV inhibitor.

Examples of DPP-IV inhibitors are described in Villhauer et al., J Med Chem (2003) 46:2774-2789, for LAF237; Ahren et al, J Clin Endocrinol Metab (2004) 89:2078-2084; Villhauer et al., J Med Chem (2002) 45:2362-2365 for NVP-DPP728; Ahren et al, Diabetes Care (2002) 25:869-875 for NVP-DPP728; Peters et al., Bioorg Med Chem Lett (2004) 14:1491-1493; Caldwell et al., Bioorg Med Chem Lett (2004) 14:1265-1268; Edmondson et al., Bioorg Med Chem Lett (2004) 14:5151-5155; and Abe et al., J Nat Prod (2004) 67:999-1004; the disclosure of each of which is herein incorporated by reference in its entirety.

Specific examples of DPP-IV inhibitors include, but are not limited to, dipeptide derivatives or dipeptide mimetics such as alanine-pyrrolidide, isoleucine-thiazolidide, and the pseudosubstrate N-valyl prolyl, O-benzoyl hydroxylamine, as described e.g. in U.S. Pat. No. 6,303,661, the disclosure of which is herein incorporated by reference in its entirety.

Examples of DPP-IV inhibitors may be found in U.S. Pat. Nos. 6,812,350, 6,803,357, 6,710,040, 6,617,340, 6,699,871, 6,573,287, 6,432,969, 6,395,767, 6,303,661, 6,242,422, 6,166,063, the disclosure of each of which is herein incorporated by reference in its entirety. Examples of DPP-IV inhibitors may be found in U.S. Pat. Appl. Nos. 2004242898, 2004180925, 2004110817, 2004106656, 2003232788, 2003216450, 2003134802, 2003125304, 2003130281, 2003119738, 2003100563, 2003119750, 2003130199, 2002183367, 2002049164, 2002006899, the disclosure of each of which is herein incorporated by reference in its entirety.

Examples of DPP-IV inhibitors may be found in International Applications WO 04/103993, WO 04/103276, WO 04/99134, WO 04/87053, WO 04/76434, WO 04/76433, WO 04/69162, WO 04/64778, WO 04/71454, WO 04/69162, WO 04/67509, WO 04/58266, WO 04/52850, WO 04/50022, WO 04/50658, WO 04/32836, WO 04/46106, WO 04/43940, WO 04/41795, WO 04/37169, WO 04/37181, WO 03/101958, WO 04/14860, WO 04/07468, WO 04/04661, WO 03/82817, WO 03/72528, WO 03/57666, WO 03/57144, WO 03/40174, WO 03/37327, WO 03/35067, WO 03/35057, WO 03/22871, WO 03/15775, WO 03/04498, WO 03/02530, WO 03/02596, WO 03/02595, WO 03/02593, WO 03/02553, WO 03/02531, WO 03/00181, WO 03/00180, WO 03/00250, WO 02/83109, WO 02/83128, WO 02/76450, WO 02/51836, WO 02/34900, WO 01/96295, WO 01/81337, WO 01/81304, WO 01/68603 WO 01/34594, WO 00/34241, WO 00/23421, WO 99/67278, WO 99/61431, WO 98/19998, WO 97/40832, EP 1480961, EP 1469873, EP 1465891, EP 1450794, EP 1446116, EP 1412357, EP 1399420, EP 1399471, EP 1399470, EP 1399469, EP 1399433, EP1406873, EP 1406622, EP 1406872, EP 1399154, EP 1377288, EP 1385508, EP 1354882, EP 1304327, EP 1296974, EP 1280797, EP 1282600, EP 1261586, EP 1215207, EP 1228061, EP 1137635, EP 1123272, EP 1082314, CA 2433090, DE 19828113, DE 19823831, DE 19616486, DE 10256264, DE 10143840, JP 2004244412, JP 2004026820, JP 2003300977, JP 2004521149, JP 2004530729, JP 2004525179, JP 2004525929, JP 2004503531, JP 2003535034, JP 2003531204, JP 2003531191, JP 2003531118, JP 2003524591, JP 2002531547, JP 2002527504, JP 2002516318, JP 2001510442, JP 2000511559, JP 2000191616, the disclosure of each of which is herein incorporated by reference in its entirety.

In one aspect of the present invention, the DPP-IV inhibitor is valine-pyrrolidide [Deacon et al, Diabetes (1998) 47:764769; the disclosure of which is herein incorporated by reference in its entirety].

In one aspect of the present invention, the DPP-IV inhibitor is 3-(L-Isoleucyl)thiazolidine (isoleucine-thiazolidide). Isoleucine-thiazolidide may be found in JP 2001510442, WO 97/40832, U.S. Pat. No. 6,303,661, and DE 19616486, the disclosure of each of which is herein incorporated by reference in its entirety. Isoleucine-thiazolidide is described as an orally active and selective DPP-IV inhibitor [Pederson et al, Diabetes (1998) 47:1253-1258; the disclosure of which is herein incorporated by reference in its entirety].

In one aspect of the present invention, the DPP-IV inhibitor is 1-[2-[5-cyanopyridin-2-yl)amino]ethylamino]acetyl-2-cyano-(S)-pyrrolidine (NVP-DPP728). NVP-DPP728 may be found in WO 98/19998 and JP 2000511559, the disclosure of each of which is herein incorporated by reference in its entirety. NVP-DPP728 is described as an orally active and selective DPP-IV inhibitor [Villhauer et al, J Med Chem (2002) 45:2362-2365].

In one aspect of the present invention, the DPP-IV inhibitor is 3(R)-Amino-1-[3-(trifluoromethyl)-5,6,7,8-tetrahydro[1,2,4]triazolo[4,3-a]pyrazin-7-yl]-4-(2,4,5-trifluorophenyl) butan-1-one (MK-0431). MK-0431 may be found in EP 1412357, WO 03/04498, U.S. Pat. No. 6,699,871, and US 2003100563, the disclosure of each of which is herein incorporated by reference in its entirety. MK-0431 is described as an orally active and selective DPP-IV inhibitor [Weber et al, Diabetes (2004) 53(Suppl.2):A151, 633-P (Abstract), the disclosure of which is herein incorporated by reference in its entirety].

In one aspect of the present invention, the DPP-IV inhibitor is (1-[[3-hydroxy-1-adamantyl)amino]acetyl]-2-cyano-(S)-pyrrolidine (LAF237). LAF237 may be found in U.S. Pat. No. 6,166,063, WO 00/34241, EP 1137635, and JP 2002531547, the disclosure of each of which is herein incorporated by reference in its entirety. LAF237 is described as an orally active and selective DPP-IV inhibitor [Villhauer et al, J Med Chem (2003) 46:2774-2789].

In one aspect of the present invention, the DPP-IV inhibitor is (1S,3S,5S)-2-[2(S)-Amino-2-(3-hydroxyadamantan-1-yl) acetyl]-2-azabicyclo[3.1.0]hexane-3-carbonitrile (BMS-477118).

In one aspect of the present invention, the DPP-IV inhibitor is selected from the right column of Table B.

In one aspect of the present invention, any one or more DPP-IV inhibitor can be excluded from any embodiment of the present invention.

In one aspect of the present invention, the DPP-IV inhibitor has an IC50 of less than about 10 µM, less than about 1 µM, less than about 100 nM, less than about 75 nM, less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM. Preferably the DPP-IV inhibitor has an IC50 of less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM.

In one aspect of the present invention, the DPP-IV inhibitor a selective DPP-IV inhibitor, wherein the selective DPP-IV inhibitor has a selectivity for human plasma DPP-IV over one or more of PPCE, DPP-II, DPP-8 and DPP-9 of at least about 10-fold, more preferably of at least about 100-fold, and most preferably of at least about 1000-fold.

In one aspect of the present invention, the DPP-IV inhibitor is orally active.

In one aspect of the present invention, the DPP-IV inhibitor is an inhibitor of human DPP-IV.

Combination of BRS-3 Agonist and DPP-IV Inhibitor

By way of illustration and not limitation, an exemplary combination of BRS-3 agonist and DPP-IV inhibitor in accordance with the present invention is provided by selecting a BRS-3 agonist from the left column of Table B and a DPP-IV inhibitor from the right column of Table B. It is expressly contemplated that each individual combination of BRS-3 agonist and DPP-IV inhibitor provided by selecting a BRS-3 agonist from the left column of Table B and a DPP-IV inhibitor from the right column of Table B is a separate embodiment within the scope of the present invention.

TABLE B

| BRS-3 Agonist | DPP-IV Inhibitor |
|---|---|
| N1-{(1R)-2-(1H-3-Indolyl)-1-[1-(2-phenylethyl)carbamoyl]ethyl}-(2S)-2-[1-(2-(4-chlorophenyl)ethyl)carboxamido]pentanediamide (Compound 1) | valine-pyrrolidide |
| N1-{(1R)-2-(1H-3-Indolyl)-1-[1-(2-phenylethyl)carbamoyl]ethyl}-(2S)-2-[(1H-2-indolylmethyl)carboxamido]pentanediamide (Compound 2) | 3-(L-Isoleucyl)thiazolidine (isoleucine-thiazolidide) |
| N1-(2-Phenylethyl)-(2R)-2-{[(1S)-1-(benzylcarboxamido)ethyl]carboxamido}-3-(1H-3-indolyl)propanamide (Compound 3) | 1-[2-[5-cyanopyridin-2-yl)amino]ethylamino]acetyl-2-cyano-(S)-pyrrolidine (NVP-DPP728) |
| N1-(2-Phenylethyl)-(2R)-2-{[(1S)-1-((4-chlorobenzyl)-carboxamido)ethyl]carboxamido}-3-(1H-3-indolyl)propanamide (Compound 4) | 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one (MK-0431) |
| N1-(2-Phenylethyl)-(2R)-2-{[(1S)-1-((1,3-benzodioxol-5-ylmethyl)carboxamido)ethyl]carboxamido}-3-(1H-3-indolyl)propanamide (Compound 5) | (1-[[3-hydroxy-1-adamantyl)amino]acetyl]-2-cyano-(S)-pyrrolidine (LAF237) |

TABLE B-continued

| BRS-3 Agonist | DPP-IV Inhibitor |
| --- | --- |
| N1-(2-Phenylethyl)-(2R)-2-{[(1S)-1-((3-pyridyl)methylcarboxamido)ethyl]carboxamido}-3-(1H-3-indolyl)propanamide (Compound 6) | (1S,3S,5S)-2-[2(S)-Amino-2-(3-hydroxyadamantan-1-yl)acetyl]-2-azabicyclo[3.1.0]hexane-3-carbonitrile (BMS-477118) |
| N1-(2-Phenylethyl)-(2R)-2-{[(1S)-1-((1,2,3,4-tetrahydro-1-isoquinolinyl)methylcarboxamido)ethyl]carboxamido}-3-(1H-3-indolyl)propanamide (Compound 7) | [1-[2(S)-Amino-3-methylbutyryl]pyrrolidin-2(R)-yl]boronic acid (PT-100) |
| N1-(2-Phenylethyl)-(2R)-2-{[(1S)-1-((1H2-indolyl)methylcarboxamido)ethyl]carboxamido}-3-(1H-3-indolyl)propanamide (Compound 8) | GSK-823093 |
| N1-(2-Phenylethyl)-(2R)-2-{[(benzyl)amino]methylcarboxamido}-3-(1H-3-indolyl)propanamide (Compound 9) | PSN-9301 |
| N1-(2-Phenylethyl)-(2R)-2-{[(4-chlorobenzyl)amino]-methylcarboxamido}-3-(1H-3-indolyl)propanamide (Compound 10) | T-6666 |
| N1-(2-Phenylethyl)-(2R)-2-{[(3-pyridyl)methylamino]-methylcarboxamido}-3-(1H-3-indolyl)propanamide (Compound 11) | SYR-322 |
| N1-(2-Phenylethyl)-(2R)-2-{[1-(2-phenylethyl)amino]-methylcarboxamido}-3-(1H-3-indolyl)propanamide (Compound 12) | SYR-619 |
| N1-(2-Phenylethyl)-(2R)-2-{[1-benzylamino)ethyl]carboxamido}-3-(1H-3-indolyl)propanamide (Compound 13) | CR-14023 |
| N1-(2-Phenylethyl)-(2R)-2-{[1-((4-chlorobenzyl)amino)ethyl]carboxamido}-3-(1H-3-indolyl)propanamide (Compound 14) | CR-14025 |
| N1-(2-Phenylethyl)-(2R)-2-{[1-(1-(2-phenylethyl)amino)ethyl]carboxamido}-3-(1H-3-indolyl)propanamide (Compound 15) | CR-14240 |
| N1-(2-Phenylethyl)-(2R)-2-{{N'-(benzoyl)hydrazino]carboxamido}-3-(1H-3-indolyl)propanamide (Compound 16) | CR-13651 |
| N1-(2-Phenylethyl)-(2R)-2-{{N'-(4-chlorobenzoyl)-hydrazino]carboxamido}-3-(1H-3-indolyl)propanamide (Compound 17) | TS-021 |
| N1-(2-Phenylethyl)-(2R)-2-{[N'-(2-(3-pyridyl)ethanoyl)hydrazino]carboxamido}-3-(1H-3-indolyl)propanamide (Compound 18) | GRC-8200 |
| N1-(2-Phenylethyl)-(2R)-2-{{N'-(2-(1,2,3,4-tetrahydro-1-isoquinolinyl)ethanoyl)hydrazino]carboxamido}-3-(1H-3-indolyl)propanamide (Compound 19) | GRC-8116 |
| N1-(2-Phenylethyl)-(2R)-2-{[N'-(2-(1H-2-indolyl)ethanoyl)hydrazino]carboxamido}-3-(1H-3-indolyl)propanamide (Compound 20) | FE107542 |
| N1-(2-Phenylethyl)-(2R)-2-{[N'-(phenylmethylene)-hydrazino]carboxamido}-3-(1H-3-indolyl)propanamide (Compound 21) | 4(S)-Fluoro-1-[2-[1-(2-hydroxyacetyl)-4-methylpiperidin-4-ylamino]acetyl]pyrrolidine-2(S)-carbonitrile fumarate |
| N1-(2-Phenylethyl)-(2R)-2-{[N'-(furan-2-ylmethylene)hydrazino]carboxamido}-3-(1H-3-indolyl)propanamide (Compound 22) | 6-[2-[2-[2(S)-Cyanoazetidin-1-yl]-2-oxoethylamino]ethylamino]pyridine-3-carbonitrile dihydrochloride |
| N1-(2-Phenylethyl)-(2R)-2-{[N'-(benzyl)hydrazino]carboxamido}-3-(1H-3-indolyl)propanamide (Compound 23) | N-(5-Chloropyridin-2-yl)-2-[4-[1-[2-(4-cyanothiazolidin-3-yl)-2-oxoethyl]hydrazino]piperidin-1-yl]acetamide tris(trifluoroacetate) |

TABLE B-continued

| BRS-3 Agonist | DPP-IV Inhibitor |
|---|---|
| N1-(2-Phenylethyl)-(2R)-2-{[N'-(4-chlorobenzyl)hydrazino]carboxamido}-3-(1H-3-indolyl)propanamide (Compound 24) | trans-4-[2-[4(R)-Cyanothiazolidin-3-yl]-2-oxoethylamino]-N,N-dimethylcyclohexanecarboxamide hydrochloride |
| N1-(2-Phenylethyl)-(2R)-2-{[N'-(2-furylmethyl)hydrazino]carboxamido}-3-(1H-3-indolyl)propanamide (Compound 25) | trans-1-[2-[4-(1,3-Dioxo-2,3-dihydro-1H-isoindol-2-yl)cyclohexylamino]acetyl]pyrrolidine-2(S)-carbonitrile hydrochloride |
| N1-(2-Phenylethyl)-(2R)-2-{[4-benzylpiperazino)methyl]carboxamido}-3-(1H-3-indolyl)propanamide (Compound 26) | 4,4-Difluoro-1-[2-[exo-8-(2-pyrimidinyl)-8-azabicyclo[3.2.1]oct-3-ylamino]acetyl]pyrrolidine-2(S)-carbonitrile |
| N1-(2-Phenylethyl)-(2R)-2-{[(4-benzylpiperidino)methyl]carboxamido}-3-(1H-3-indolyl)propanamide (Compound 27) | exo-3-[2-[8-(2-Pyrimidinyl)-8-azabicyclo[3.2.1]oct-3-ylamino]acetyl]thiazolidine-4(R)-carbonitrile |
| [D-Tyr$^6$,(R)-Apa$^{11}$,Phe$^{13}$,Nle$^{14}$]Bombesin(6-14) (Compound 28) | 3(R)-Amino-1-(8-chloro-1,2,3,4-tetrahydropyrazino[1,2-a]benzimidazol-2-yl)-4-(2,5-difluorophenyl)butan-1-one trifluoroacetate |
| [D-Tyr$^6$,(S)-Apa$^{11}$,Phe$^{13}$,Nle$^{14}$]Bombesin(6-14) (Compound 29) | 3(R)-Amino-4-(2,5-difluorophenyl)-1-[2-(4-fluorophenyl)-4,5,6,7-tetrahydrothiazolo[4,5-c]pyridin-5-yl]butan-1-one |
| [D-Tyr$^6$,(R)-Apa$^{11}$-4Cl,Phe$^{13}$,Nle$^{14}$]Bombesin(6-14) (Compound 30) | 2-[4-[2-[3(R)-Amino-4-(2-fluorophenyl)butyryl]-1,2,3,4-tetrahydroisoquinolin-3-ylcarboxamidomethyl]phenyl]acetic acid |
| Ac-Phe-Trp-Ala-His(τBzl)-Nip-Gly-Arg-NH$_2$ (Compound 31) | 1-(2-Benzothiazolyl)-1-[1-[(2S,3aS,7aS)-perhydroindol-2-ylcarbonyl]pyrrolidin-2(S)-yl]methanone hydrochloride |
| Ac-Phe-Trp-Ala-His(τBzl)-βAla-His-Arg-NH$_2$ (Compound 32) | trans-N-[4-[1(S)-Amino-2-[3(S)-fluoropyrrolidin-1-yl]-2-oxoethyl]cyclohexyl]-2,4-difluorobenzenesulfonamide |
| Ac-Phe-Trp-Ala-Val-βAla-His-Arg-Trp-NH$_2$ (Compound 33) | (1S,3S,5S)-2-[2(S)-Amino-4,4-dimethylpentanoyl]-2-azabicyclo[3.1.0]hexane-3(S)-carbonitrile trifluoroacetate |
| [D-Tyr$^6$,βAla$^{11}$,Phe$^{13}$,Nle$^{14}$]Bombesin(6-14) (Compound 34) | 2-[7-(2-Butynyl)-1-(2-phenylethyl)-8-(1-piperazinyl)xanthin-3-yl]-N-(2-propynyl)acetamide hydrochloride |

Additionally, compounds of the invention, including those illustrated in TABLE B, encompass all pharmaceutically acceptable salts, solvates, and hydrates thereof. See, e.g., Berge et al (1977), Journal of Pharmaceutical Sciences 66:1-19; and Polymorphism in Pharmaceutical Solids (1999) Brittain, ed., Marcel Dekker, Inc.; the disclosure of each of which is herein incorporated by reference in its entirety.

As relates to the combination therapy described above, the compounds according to the invention can be administered in any suitable way. Suitable routes of administration include oral, nasal, rectal, transmucosal, transdermal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other suitable routes of administration are aerosol and depot formulation. Sustained release formulations, particularly depot, of the invented medicaments are expressly contemplated. In certain preferred embodiments, the compounds according to the present invention are administered orally. The compounds according to the present invention can be made up in solid or liquid form, such as tablets, capsules, powders, syrups, elixirs and the like, aerosols, sterile solutions, suspensions or emulsions, and the like. In certain embodiments, one or both of the BRS-3 agonist and the DPP-IV inhibitor are administered orally.

Formulations for oral administration may be in the form of aqueous solutions and suspensions, in addition to solid tablet and capsule formulations. The aqueous solutions and suspensions may be prepared from sterile powders or granules. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants are well and widely known in the art.

It will be appreciated that the BRS-3 agonist and the DPP-IV inhibitor may be present as a combined preparation for simultaneous, separate or sequential use for the treatment or prevention of diabetes or a condition related thereto. Such combined preparations may be, for example, in the form of a twin pack.

It will therefore be further appreciated that the invention contemplates a product comprising or consisting essentially of a BRS-3 agonist and a DPP-IV inhibitor as a combined preparation for simultaneous, separate or sequential use in the prevention or treatment of diabetes or a condition related thereto.

A combination of the present invention comprising or consisting essentially of a BRS-3 agonist and a DPP-IV inhibitor can be prepared by mixing the BRS-3 agonist and the DPP-IV inhibitor either all together or independently with a pharmaceutically acceptable carrier, excipient, binder, dilutent, etc. as described herein, and administering the mixture or mixtures either orally or non-orally as a pharmaceutical composition(s).

It will therefore be further appreciated that the BRS-3 agonist and the DPP-IV inhibitor or pharmaceutical composition can be administered in separate doseage forms or in a single doseage form.

It is further appreciated that when the BRS-3 agonist and the DPP-IV inhibitor are in separate doseage forms, BRS-3 agonist and DPP-IV inhibitor can be administered by different routes.

Pharmaceutical compositions of the BRS-3 agonist and DPP-IV inhibitor, either individually or in combination, may be prepared by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries which facilitate processing of the active compounds into preparations which can be used pharmaceutically. Suitable pharmaceutically acceptable carriers are available to those in the art [see, e.g., Remington: The Science and Practice of Pharmacy, (Gennaro et al., eds.), 20$^{th}$ Edition, 2000, Lippincott Williams & Wilkins; and Handbook of Pharmaceutical Excipients (Rowe et al., eds), 4$^{th}$ Edition, 2003, Pharmaceutical Press; the disclosure of each of which is herein incorporated by reference in its entirety]. Proper formulation is dependent upon the route of administration chosen. The term "carrier" material or "excipient" material herein means any substance, not itself a therapeutic agent, used as a carrier and/or dilutent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improved appearance of the composition. Acceptable excipients include stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax cocoa butter or powder, polymers, such as polyvinyl-pyrrolidone, polyvinyl alcohol, and polyethylene glycols, and other pharmaceutically acceptable materials. The components of the pharmaceutical composition can be encapsulated or tableted for convenient administration.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When the BRS-3 agonist and the DPP-IV inhibitor are in separate dosage forms, it is understood that a pharmaceutically acceptable carrier used for the BRS-3 agonist formulation need not be identical to a pharmaceutically acceptable carrier used for the DPP-IV inhibitor formulation.

Dragee cores are provided with suitable coatings. For this purpose, concentrated sugar solutions may be used which may optionally contain gum Arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mon-, di- or triglycerides. Stabilizers may be added in these formulations, also.

Additionally, the BRS-3 agonist and DPP-IV inhibitor may be delivered using a sustained-release system. Various sustained-release materials have been established and are well known to those skilled in the art. Sustained-release tablets or capsules are particularly preferred. For example, a time delay material such as glyceryl monostearate or glyceryl distearate may be employed. The dosage form may also be coated by the techniques described in the U.S. Pat. Nos. 4,256,108, 4,166, 452, and 4,265,874 to form osmotic therapeutic tablets for controlled release.

It is expressly contemplated that a combination therapy of the present invention may be administered or provided alone or in combination with one or more other pharmaceutically or physiologically acceptable compound. In one aspect of the present invention, the other pharmaceutically or physiologically acceptable compound is not a BRS-3 agonist and is not a DPP-IV inhibitor.

In one aspect of the present invention, the other pharmaceutically or physiologically acceptable compound is a pharmaceutical agent selected from the group consisting of sulfonylurea (e.g., glibenclamide, glipizide, gliclazide, glimepiride), meglitinide (e.g., repaglinide, nateglinide), biguanide (e.g., metformin), alpha-glucosidase inhibitor (e.g., acarbose, epalrestat, miglitol, voglibose), thizaolidinedione (e.g., rosiglitazone, pioglitazone), insulin analog (e.g., insulin lispro, insulin aspart, insulin glargine), chromium picolinate/biotin, and biological agent (e.g., adiponectin or a fragment comprising the C-terminal globular domain thereof, or a multimer of adiponectin or said fragment thereof; or an agonist of adiponectin receptor AdipoR1 or AdipoR2, preferably wherein said agonist is orally active). In one aspect of the present invention, the pharmaceutical agent is metformin. In one aspect of the present invention, the pharmaceutical agent is an agonist to adiponectin receptor AdipoR1 or AdipoR2, preferably wherein the agonist is orally active.

In one aspect of the present invention, the other pharmaceutically or physiologically acceptable compound is an anti-obesity agent such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion). In some embodiments, the anti-obesity agent is selected from the group consisting of orlistat, sibutramine, bromocriptine, ephedrine, leptin, and pseudoephedrine.

In a combination therapy according to the present invention, the BRS-3 agonist according to the present invention and the DPP-IV inhibitor according to the present invention can be administered simultaneously or at separate intervals. When administered simultaneously the BRS-3 agonist and the DPP-IV inhibitor can be incorporated into a single pharmaceutical composition or into separate compositions, e.g., the BRS-3 agonist in one composition and the DPP-IV inhibitor in another composition. Each of these compositions may be formulated with common excipients, diluents or carriers, and compressed into tablets, or formulated elixirs or solutions; and as sustained relief dosage forms and the like. The BRS-3 agonist and DPP-IV inhibitor may be administered via different routes. For example, the BRS-3 agonist may be administered orally via tablet and the DPP-IV inhibitor may be administered via inhalation.

When separately administered, therapeutically effective amounts of the BRS-3 agonist and the DPP-IV inhibitor according to the present invention are administered on a different schedule. One may be administered before the other as long as the time between the two administrations falls within a therapeutically effective interval. A therapeutically effective interval is a period of time beginning when one of either (a) the BRS-3 agonist or (b) the DPP-IV inhibitor is administered to a mammal and ending at the limit of the beneficial effect in the treatment of the combination of (a) and (b).

In one aspect, the present invention features a pharmaceutical composition comprising or consisting essentially of a combination of an amount of a BRS-3 agonist according to the present invention and an amount of a DPP-IV inhibitor according to the present invention, together with at least one pharmaceutically acceptable carrier.

In one aspect, the present invention features a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in lowering a blood glucose level in a subject. In certain embodiments, the blood glucose level is an elevated blood glucose level.

In one aspect, the present invention features a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in lowering a blood glucose level in a subject, and wherein the amount of the BRS-3 agonist alone and the amount of the DPP-IV inhibitor alone are therapeutically ineffective in lowering the blood glucose level in the subject. In certain embodiments, the blood glucose level is an elevated blood glucose level.

In one aspect, the present invention features a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in lowering a blood glucose level in a subject, and wherein the effect is a synergistic effect. In certain embodiments, the blood glucose level is an elevated blood glucose level.

In one aspect, the present invention relates to a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in lowering a blood glucose level in a subject, wherein the effect is a synergistic effect, and wherein the amount of the BRS-3 agonist alone and the amount of the DPP-IV inhibitor alone are therapeutically ineffective in lowering the blood glucose level in the subject. In certain embodiments, the blood glucose level is an elevated blood glucose level.

In one aspect, the present invention relates to a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in lowering a blood glucose level in a subject, wherein the effect given by the combination of the amount of the BRS-3 agonist and the amount of the DPP-IV inhibitor is greater than the effect given by the amount of the BRS-3 agonist alone and the effect given by the amount of the DPP-IV inhibitor alone. In certain embodiments, the blood glucose level is an elevated blood glucose level.

In one aspect, the present invention features a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in increasing a blood GLP-1 level in a subject.

In one aspect, the present invention features a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in increasing a blood GLP-1 level in a subject, and wherein the amount of the BRS-3 agonist alone and the amount of the DPP-IV inhibitor alone are therapeutically ineffective in increasing a blood GLP-1 level in the subject.

In one aspect, the present invention features a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in increasing a blood GLP-1 level in a subject, and wherein the effect is a synergistic effect.

In one aspect, the present invention relates to a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in increasing a blood GLP-1 level in a subject, wherein the effect is a synergistic effect, and wherein the amount of the BRS-3 agonist alone and the amount of the DPP-IV inhibitor alone are therapeutically ineffective in increasing a blood GLP-1 level in the subject.

In one aspect, the present invention relates to a pharmaceutical composition comprising or consisting essentially of a combination of an amount of a BRS-3 agonist according to the present invention and an amount of a DPP-IV inhibitor according to the present invention, together with at least one pharmaceutically acceptable carrier. The present invention also relates to a dosage form of the pharmaceutical composition wherein the BRS-3 agonist and the DPP-IV inhibitor are in amounts sufficient to give an effect in increasing a blood GLP-1 level in a subject, wherein the effect given by the combination of the amount of the BRS-3 agonist and the amount of the DPP-IV inhibitor is greater than the effect given by the amount of the BRS-3 agonist alone and the effect given by the amount of the DPP-IV inhibitor alone.

Pharmaceutical compositions suitable for use in the present invention include compositions wherein the active ingredients are contained in an amount to achieve their intended purpose. In some embodiments, a pharmaceutical composition of the present invention is understood to be useful for treating or preventing diabetes and conditions related thereto. Diabetes and conditions related thereto are according to the present invention. In some embodiments, a pharmaceutical composition of the present invention is understood to be useful for treating or preventing a condition ameliorated by increasing a blood GLP-1 level. Conditions ameliorated by increasing a blood GLP-1 level are according to the present invention.

In certain embodiments of the combination therapy of the present invention, the amount of BRS-3 agonist according to the present invention and the amount of DPP-IV inhibitor according to the present invention are provided in amounts to give a synergistic effect in lowering a blood glucose level in a subject. In certain embodiments, the blood glucose level is an elevated blood glucose level. Determination of the amounts of BRS-3 agonist and DPP-IV inhibitor providing a synergistic effect in lowering blood glucose level in a subject is well within the capability of those skilled in the art, especially in light of the detailed disclosure provided herein. In one embodiment of the combination therapy of the present invention, the amount of BRS-3 agonist according to the present invention and the amount of DPP-IV inhibitor according to the present invention are provided in amounts to give a synergistic effect in lowering a blood glucose level in a subject, wherein the amount of the BRS-3 agonist alone and the amount of the DPP-IV inhibitor alone are therapeutically ineffective in lowering the blood glucose level in the subject. In certain embodiments, the blood glucose level is an elevated blood glucose level. Determination of the amounts of BRS-3 agonist and DPP-IV inhibitor providing a synergistic effect in lowering blood glucose level in a subject, wherein the amount of the BRS-3 agonist alone and the amount of the DPP-IV inhibitor alone are therapeutically ineffective in lowering blood glucose level in the subject, is well within the capability of those skilled in the art, especially in light of the detailed disclosure provided herein.

In certain embodiments of the combination therapy of the present invention, the amount of BRS-3 agonist according to the present invention and the amount of DPP-IV inhibitor according to the present invention are provided in amounts to give a synergistic effect in increasing a blood GLP-1 level in a subject. Determination of the amounts of BRS-3 agonist and DPP-IV inhibitor providing a synergistic effect in increasing a blood GLP-1 level in a subject is well within the capability of those skilled in the art, especially in light of the detailed disclosure provided herein. In one embodiment of the combination therapy of the present invention, the amount of BRS-3 agonist according to the present invention and the amount of DPP-IV inhibitor according to the present invention are provided in amounts to give a synergistic effect in increasing a blood GLP-1 level in a subject, wherein the amount of the BRS-3 agonist alone and the amount of the DPP-IV inhibitor alone are therapeutically ineffective in increasing a blood GLP-1 level in the subject. Determination of the amounts of BRS-3 agonist and DPP-IV inhibitor providing a synergistic effect in increasing a blood GLP-1 level in a subject, wherein the amount of the BRS-3 agonist alone and the amount of the DPP-IV inhibitor alone are therapeutically ineffective in increasing a blood GLP-1 level in the subject, is well within the capability of those skilled in the art, especially in light of the detailed disclosure provided herein.

The data obtained from animal studies, including but not limited to studies using mice, rats, rabbits, pigs, and non-human primates, can be used in formulating a range of dosage for use in humans. In general, one skilled in the art understands how to extrapolate in vivo data obtained in an animal model system to another, such as a human. In some circumstances, these extrapolations may merely be based on the weight of the animal model in comparison to another, such as a human; in other circumstances, these extrapolations are not simply based on weights but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

An exemplary and preferred animal model system is oral glucose tolerance test (oGTT) in mice (see, Example 1). In this model, by way of illustration and not limitation, an amount of a BRS-3 agonist alone or a DPP-IV inhibitor alone which is therapeutically ineffective is an amount of the BRS-3 agonist alone or the DPP-IV inhibitor alone producing an Area Under Curve (AUC) inhibition of glycemic excursion less than or equal to about 30%, less than about 25%, less than about 20%, less than about 15%, less than about 10%, or less than about 5%, more preferably less than about 25%, less than about 20%, less than about 15%, less than about 10%, or less than about 5%. In this model, by way of illustration and not limitation, an amount of a BRS-3 agonist alone or a DPP-IV inhibitor alone which is therapeutically ineffective is an amount of the BRS-3 agonist alone or the DPP-IV inhibitor alone producing an Area Under Curve (AUC) inhibition of glycemic excursion about 0-30%, about 0-25%, about 0-20%, about 0-15%, about 0-10%, or about 0-5%, more preferably about 0-25%, about 0-20%, about 0-15%, about 0-10%, or about 0-5%. In this model, by way of illustration and not limitation, a therapeutically effective amount of a combination of a BRS-3 agonist and a DPP-IV inhibitor in accordance with the present invention is an amount of the combination producing an Area Under Curve (AUC) inhibition of glycemic excursion greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, or greater than about 95%, more preferably greater than about 35%, greater than about 40%, greater than about 45%, greater than about 50%, greater than about 55%, greater than about 60%, greater than about 65%, greater than about 70%, or greater than about 75%, greater than about 80%, greater than about 85%, greater than about 90%, or greater than about 95%.

Dosage amount and interval may be adjusted in order to provide a synergistic effect in lowering a blood glucose level in the subject in accordance with the present invention or to provide a synergistic effect in increasing a blood GLP-1 level in the subject in accordance with the present invention. In certain embodiments, the blood glucose level is an elevated blood glucose level. It will be appreciated that the exact dosage of a BRS-3 agonist or DPP-IV inhibitor in accordance with the present invention will vary depending on the combination of the BRS-3 agonist and DPP-IV inhibitor, its potency, the mode of administration, the age and weight of the patient and the severity of the condition to be treated. The exact formulation, route of administration and dosage can be chosen by the individual physician in view of the patient's condition. By way of illustration and not limitation, an amount of BRS-3 agonist or DPP-IV inhibitor providing a synergistic effect in lowering a blood glucose level in the subject in accordance with the present invention or providing a synergistic effect in increasing a blood GLP-1 level in the subject in accordance with the present invention is less than about 0.001 mg/kg body weight, less than about 0.005 mg/kg body weight, less than about 0.01 mg/kg body weight, less than about 0.05 mg/kg body weight, less than about 0.1 mg/kg body weight, less than about 0.5 mg/kg body weight, less than about 1 mg/kg body weight, less than about 5 mg/kg body weight, less than about 10 mg/kg body weight, less than about 50 mg/kg body weight, or less than about 100 mg/kg body weight. In certain embodiments, the blood glucose level is an elevated blood glucose level. In some embodiments, an amount of BRS-3 agonist or DPP-IV inhibitor providing a synergistic effect in lowering a blood glucose level in the subject in accordance with the present invention or providing a synergistic effect in increasing a blood GLP-1 level in the subject in accordance with the present invention is less than about 0.001-100 mg/kg body weight, less than about 0.001-50 mg/kg body weight, less than about 0.001-10 mg/kg body weight, less than about 0.001-5 mg/kg body weight, less than about 0.001-1 mg/kg body weight, less than about 0.001 to 0.5 mg/kg body weight, less than about 0.001-0.1 mg/kg body weight, less than about 0.001-0.05 mg/kg body weight, less than about 0.001-0.01 mg/kg body weight, or less than about 0.001-0.005 mg/kg body weight. In certain embodiments, the blood glucose level is an elevated blood glucose level. In some embodiments, an amount of BRS-3 agonist or DPP-IV inhibitor providing a synergistic effect in lowering a blood glucose level in the subject in accordance with the present invention or providing a synergistic effect in increasing a blood GLP-1 level in the subject in accordance with the present invention is about 0.001-100 mg/kg body weight, about 0.001-50 mg/kg body weight, about 0.001-10 mg/kg body weight, about 0.001-5 mg/kg body weight, about 0.001 to 1 mg/kg body weight, about 0.001-0.5 mg/kg body weight, about 0.001-0.1 mg/kg body weight, about 0.001-0.05 mg/kg body weight, about 0.001-0.01 mg/kg body weight, or about 0.001-0.005 mg/kg body weight. In certain embodiments, the blood glucose level is an elevated blood glucose level.

An additional exemplary and preferred animal model system is increase of a blood GLP-1 level after glucose challenge in mice (see, Example 15).

Dosage amount and interval may be adjusted individually to provide plasma levels of BRS-3 agonist according to the present invention and DPP-IV inhibitor according to the present invention which provide a synergistic effect in lowering a blood glucose level in the subject according to the present invention or provide a synergistic effect in increasing a blood GLP-1 level in the subject according to the present invention. In certain embodiments, the blood glucose level is an elevated blood glucose level. Dosage intervals can also be determined using the value for a selected range of BRS-3 agonist concentration or the value for a selected range of DPP-IV inhibitor concentration providing a synergistic effect in lowering a blood glucose level in the subject according to the present invention or providing a synergistic effect in increasing a blood GLP-1 level in the subject according to the present invention. In certain embodiments, the blood glucose level is an elevated blood glucose level. BRS-3 agonist and DPP-IV inhibitor should be administered using a regimen that maintains plasma levels within the selected range of BRS-3 agonist concentration and DPP-IV inhibitor concentration, respectively, for 10-90% of the time, preferably between 30-99% of the time, and most preferably between 50-90% of the time. In cases of local administration or selective uptake, the range of BRS-3 agonist concentration or the range of DPP-IV inhibitor concentration providing a synergistic effect in lowering a blood glucose level in the subject according to the present invention or providing a synergistic effect in increasing a blood GLP-1 level in the subject according to the present invention may not be related to plasma concentration. In certain embodiments, the blood glucose level is an elevated blood glucose level.

The amount of composition administered will, of course, be dependent on the subject being treated, on the subject's weight, the severity of the affliction, the manner of administration, and the judgement of the prescribing physician.

In one aspect, the present invention accordingly features a method of treating or preventing diabetes or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention.

In one aspect, the present invention relates to a method of treating or preventing diabetes or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in lowering a blood glucose level in the subject. In certain embodiments, the blood glucose level is an elevated blood glucose level.

In one aspect, the present invention relates to a method of treating or preventing diabetes or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in lowering a blood glucose level in the subject, and wherein the amount of the BRS-3 agonist alone and the amount of the DPP-IV inhibitor alone are therapeutically ineffective in lowering the blood glucose level in the subject. In certain embodiments, the blood glucose level is an elevated blood glucose level.

In one aspect, the present invention relates to a method of treating or preventing diabetes or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in lowering a blood glucose level in the subject, and wherein the effect is a synergistic effect. In certain embodiments, the blood glucose level is an elevated blood glucose level.

In one aspect, the present invention relates to a method of treating or preventing diabetes or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in lowering a blood glucose level in the subject, wherein the effect is a synergistic effect, and wherein the amount of the BRS-3 agonist alone and the amount of the DPP-IV inhibitor alone are therapeutically ineffective in lowering the blood glucose level in the subject. In certain embodiments, the blood glucose level is an elevated blood glucose level.

In one aspect, the present invention relates to a method of treating or preventing diabetes or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in lowering a blood glucose level in the subject, wherein the effect given by the combination of the amount of the BRS-3 agonist and the amount of the DPP-IV inhibitor is greater than the effect given by the amount of the BRS-3 agonist alone and the effect given by the amount of the DPP-IV inhibitor alone. In certain embodiments, the blood glucose level is an elevated blood glucose level.

A combination therapy of the present invention is useful in treating or preventing diabetes or a condition related thereto in a mammal, including and most preferably in a human. In some embodiments, diabetes is Type 1 diabetes. In some preferred embodiments, diabetes is Type 2 diabetes. A condition related to diabetes includes, but is not limited to, hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity. It is understood that conditions related to diabetes can be included in embodiments individually or in any combination.

In one aspect, the present invention accordingly features a method of reducing body mass comprising administering to a subject in need thereof a therapeutically effective amount of a composition comprising or consisting essentially of an amount of a BRS-3 agonist according to the present invention and an amount of a DPP-IV inhibitor according to the present invention.

In one aspect, the present invention relates to a method of reducing body mass comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject.

In one aspect, the present invention relates to a method of reducing body mass comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, and wherein the amount of the BRS-3 agonist alone and the amount of the DPP-IV inhibitor alone are therapeutically ineffective in increasing a blood GLP-1 level in the subject.

In one aspect, the present invention relates to a method of reducing body mass comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, and wherein the effect is a synergistic effect.

In one aspect, the present invention relates to a method of reducing body mass comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, wherein the effect is a synergistic effect, and wherein the amount of the BRS-3 agonist alone and the amount of the DPP-IV inhibitor alone are therapeutically ineffective in increasing a blood GLP-1 level in the subject.

In one aspect, the present invention relates to a method of reducing body mass comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, wherein the effect given by the combination of the amount of the BRS-3 agonist and the amount of the DPP-IV inhibitor is greater than the effect given by the amount of the BRS-3 agonist alone and the effect given by the amount of the DPP-IV inhibitor alone.

In one aspect, the present invention accordingly features a method of treating or preventing obesity or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention.

In one aspect, the present invention relates to a method of treating or preventing obesity or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject.

In one aspect, the present invention relates to a method of treating or preventing obesity or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, and wherein the amount of the BRS-3 agonist alone and the amount of the DPP-IV inhibitor alone are therapeutically ineffective in increasing a blood GLP-1 level in the subject.

In one aspect, the present invention relates to a method of treating or preventing obesity or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, and wherein the effect is a synergistic effect.

In one aspect, the present invention relates to a method of treating or preventing obesity or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, wherein the effect is a synergistic effect, and wherein the amount of the BRS-3 agonist alone and the amount of the DPP-IV inhibitor alone are therapeutically ineffective in increasing a blood GLP-1 level in the subject.

In one aspect, the present invention relates to a method of treating or preventing obesity or a condition related thereto comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, wherein the effect given by the combination of the amount of the BRS-3 agonist and the amount of the DPP-IV inhibitor is greater than the effect given by the amount of the BRS-3 agonist alone and the effect given by the amount of the DPP-IV inhibitor alone.

A combination therapy of the present invention is useful in treating or preventing obesity or a condition related thereto in a mammal, including and most preferably in a human. A condition related to obesity includes, but is not limited to, hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, Type 2 diabetes, dyslipidemia, hyperandrogenemia in women, polycystic ovarian syndrome, dysmenorrhea, infertility, pregnancy complications, and male hypogonadism. In certain embodiments, the condition related to obesity is selected from the group consisting of hypertension, congestive cardiomyopathy, coronary heart disease, stroke, dyslipidemia, metabolic syndrome, and Type 2 diabetes. It is understood that conditions related to obesity can be included in embodiments individually or in any combination.

In one aspect, the present invention accordingly features a method of treating or preventing a condition ameliorated by increasing a blood GLP-1 level comprising administering to a subject in need thereof a therapeutically effective amount of a composition comprising or consisting essentially of an amount of a BRS-3 agonist according to the present invention and an amount of a DPP-IV inhibitor according to the present invention.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, and wherein the amount of the BRS-3 agonist alone and the amount of the DPP-IV inhibitor alone are therapeutically ineffective in increasing a blood GLP-1 level in the subject.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, and wherein the effect is a synergistic effect.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, wherein the effect is a synergistic effect, and wherein the amount of the BRS-3 agonist alone and the amount of the DPP-IV inhibitor alone are therapeutically ineffective in increasing a blood GLP-1 level in the subject.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a BRS-3 agonist according to the present invention and an amount of a DPP-IV inhibitor according to the present invention. In a related aspect, the present invention features said method wherein the BRS-3 agonist and the DPP-IV inhibitor are administered in amounts sufficient to give an effect in increasing a blood GLP-1 level in the subject, wherein the effect given by the combination of the amount of the BRS-3 agonist and the amount of the DPP-IV inhibitor is greater than the effect given by the amount of the BRS-3 agonist alone and the effect given by the amount of the DPP-IV inhibitor alone.

A combination therapy of the present invention is useful in treating or preventing a condition ameliorated by increasing a blood GLP-1 level in a mammal, including and most preferably in a human. A condition ameliorated by increasing a blood GLP-1 level includes, but is not limited to, diabetes, a condition related to diabetes, myocardial infarction, learning impairment, memory impairment, and a neurodegenerative disorder, wherein a condition related to diabetes includes, but is not limited to, hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity, wherein a neurodegenerative disorder includes, but is not limited to, excitotoxic brain damage caused by severe epileptic seizures, Alzheimer's disease, Parkinson's disease, Huntington's disease, prion-associated disease, motor-neuron disease, traumatic brain injury, spinal cord injury, and peripheral neuropathy. In some embodiments, diabetes is Type 1 diabetes. In some preferred embodiments, diabetes is Type 2 diabetes. It is understood that conditions ameliorated by increasing a blood GLP-1 level can be included in embodiments individually or in any combination.

Without further elaboration, it is believed that one skilled in the art can, using the preceding description, practice the present invention to its fullest extent. The foregoing detailed description is given for clearness of understanding only, and no unnecessary limitation should be understood therefrom, as modifications within the scope of the invention may become apparent to those skilled in the art.

Recombinant DNA techniques relating to the subject matter of the present invention and well known to those of ordinary skill in the art can be found, e.g, in Sambrook et al., *Molecular Cloning: A Laboratory Manual* (2001) Cold Spring Harbor Laboratory; the disclosure of which is hereby incorporated by reference in its entirety.

Throughout this application, various publications, patents and patent applications are cited. The disclosures of these publications, patents and patent applications referenced in this application are herein incorporated by reference in their entirety into the present disclosure. Citation herein by Applicant of a publication, patent, or patent application is not an admission by Applicant of said publication, patent, or patent application as prior art.

EXAMPLES

Without further elaboration, it is believed that one skilled in the art can, using the preceding description, practice the present invention to its fullest extent. The following detailed examples are to be construed as merely illustrative, and not limitations of the preceding disclosure in any way whatsoever. Those skilled in the art will promptly recognize appropriate variations from the procedures.

Example 1

Full-Length Cloning of Endogenous Human Brs-3

Polynucleotide encoding endogenous human BRS-3 was cloned by RT-PCR using the BRS-3 specific primers
5'-ACAGAATTCAGAAGAAATGGCTCAAAGGCA-3'
  (SEQ ID NO:3; sense with EcoRI site, ATG as initiation codon) and
5'-CATGGATCCTTGAAAAGCTAGAATCTGTCC-3'
  (SEQ ID NO:4; antisense with BamHI site, CTA as antisense of stop codon)
and human uterus cDNA (Clontech) as template. TaqPlus Precision™ DNA polymerase (Stratagene) was used for amplification by the following cycle with step 2 to step 4 repeated 25 times:
94° C., 3 minutes; 94° C., 1 minute; 56° C., 1 minute; 72° C., 1 minute 20 sec; 72° C., 10 minutes.
A 1.23 Kb PCR fragment of predicted size was isolated, digested with EcoRI and BamHI, and cloned into the pCMV expression vector and sequenced using the T7 DNA sequenase kit (Amersham). See, SEQ ID NO:1 for nucleic acid sequence and SEQ ID NO:2 for the deduced amino acid sequence.

Example 2

Receptor Expression

Although a variety of cells are available to the art for the expression of G protein-coupled receptors, it is most preferred that mammalian cells or melanophores be utilized. The following are illustrative; those of ordinary skill in the art are credited with the ability to determine those techniques that are preferentially beneficial for the needs of the artisan. See, e.g., Example 6, infra, as it relates to melanophores.

a. Transient Transfection

On day one, $6 \times 10^6$/10 cm dish of 293 cells are plated out. On day two, two reaction tubes are prepared (the proportions to follow for each tube are per plate): tube A is prepared by mixing 4 µg DNA (e.g., pCMV vector; pCMV vector with receptor cDNA, etc.) in 0.5 ml serum free DMEM (Gibco BRL); tube B is prepared by mixing 24 µl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1×PBS, followed by addition of 5 ml serum free DMEM. 1 ml of the transfection mixture is added to the cells, followed by incubation for 4 hrs at 37° C./5% CO$_2$. The transfection mixture is removed by aspiration, followed by the addition of 10 ml of DMEM/10% Fetal Bovine Serum. Cells are incubated at 37° C./5% CO$_2$. After 48 hr incubation, cells are harvested and utilized for analysis.

b. Stable Cell Lines

Approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 µg of DNA (e.g., pCMV vector with receptor cDNA). The 12 µg of DNA is combined with 60 µl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 µg of DNA (e.g., pCMV vector with receptor cDNA). The 12 µg of DNA is combined with 60 µl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 µg/ml. The transfected cells now undergo selection for positively transfected cells containing the G418 resistance gene. The medium is replaced every four to five days as selection occurs. During selection, cells are grown to create stable pools, or split for stable clonal selection.

Example 3

Assays for Screening Candidate Compounds as Brs-3 Agonists

A variety of approaches are available for screening candidate compounds as BRS-3 agonists. The following are illustrative; those of ordinary skill in the art are credited with the ability to determine those techniques that are preferentially beneficial for the needs of the artisan. Assays for screening compounds as agonists of a G protein-coupled receptor are well known to the skilled artisan (see, e.g., International Application WO 02/42461).

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay is generic and has application to drug discovery at all G protein-coupled receptors.

Membrane Preparation

In some embodiments, membranes comprising a G protein-coupled receptor of the invention and for use in the identification of candidate compounds as, e.g., agonists of the receptor, are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM MgCl$_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension). This is referred to herein as "Membrane Protein".

Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 µl Binding Buffer. Thereafter, 10 µl of Bradford Protein Standard (1 mg/ml) will be added to each tube, and 10 µl of membrane Protein will then be added to just one tube (not the blank). Thereafter, 200 µl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595.

Identification Assay a. Materials

GDP Buffer consisted of 37.5 ml Binding Buffer and 2 mg GDP (Sigma, cat. no. G-7127), followed by a series of dilutions in Binding Buffer to obtain 0.2 µM GDP (final concentration of GDP in each well was 0.1 µM GDP); each well comprising a candidate compound, has a final volume of 200 µl consisting of 100 µl GDP Buffer (final concentration, 0.1 µM GDP), 50 µl Membrane Protein in Binding Buffer, and 50 µl [$^{35}$S]GTPγS (0.6 nM) in Binding Buffer (2.5 µl [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the Target GPCR, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 µg/well). Thereafter, 100 µl GDP Buffer was added to each well of a Wallac Scintistrip™ (Wallac). A Sul pin-tool will then be used to transfer 5 µl of a candidate compound into such well (i.e., 5 µl in total assay volume of 200 µl is a 1:40 ratio such that the final screening concentration of the candidate compound is 10 µM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 µl of Membrane Protein will be added to each well (a control well comprising membranes without the Target GPCR was also utilized), and pre-incubated for 5-10 minutes at room temperature. Thereafter, 50 µl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer's instructions).

2. Adenylyl Cyclase Assay

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

In certain embodiments, a modified Flash Plate™ Adenylyl Cyclase kit (New England Nuclear; Cat. No. SMP004A) is utilized for identification of candidate compounds as, e.g., BRS-3 agonists in accordance with the following protocol.

Cells transfected with a G protein-coupled receptor of the invention are harvested approximately three days after transfection. Membranes are prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM MgCl$_2$, to yield a final protein concentration of 0.60 mg/ml (the resuspended membranes are placed on ice until use).

cAMP standards and Detection Buffer (comprising 2 µCi of tracer {[$^{125}$I]cAMP (100 µl) to 11 ml Detection Buffer] are prepared and maintained in accordance with the manufacturer's instructions. Assay Buffer was prepared fresh for screening and contained 20 mM HEPES, pH 7.4, 10 mM $MgCl_2$, 20 mM phospocreatine (Sigma), 0.1 units/ml creatine phosphokinase (Sigma), 50 µM GTP (Sigma), and 0.2 mM ATP (Sigma); Assay Buffer was then stored on ice until utilized.

Candidate compounds are added, preferably, to e.g. 96-well plate wells (3 µl/well; 12 µM final assay concentration), together with 40 µl Membrane Protein (30 µg/well) and 50 µl of Assay Buffer. This admixture was then incubated for 30 minutes at room temperature, with gentle shaking.

Following the incubation, 100 µl of Detection Buffer is added to each well, followed by incubation for 2-24 hours. Plates are then counted in a Wallac MicroBeta™ plate reader using "Prot. #31" (as per manufacturer's instructions).

3. Reporter-Based Assays a. CRE-Luc Reporter Assay 293 and 293T cells are plated-out on 96 well plates at a density of $2 \times 10^4$ cells per well and were transfected using Lipofectamine Reagent (BRL) the following day according to manufacturer instructions. A DNA/lipid mixture is prepared for each 6-well transfection as follows: 260 ng of plasmid DNA in 100 µl of DMEM is gently mixed with 2 µl of lipid in 100 µl of DMEM (the 260 ng of plasmid DNA consists of 200 ng of a 8×CRE-Luc reporter plasmid, 50 ng of pCMV comprising a G protein-coupled receptor of the invention or pCMV alone, and 10 ng of a GPRS expression plasmid [GPRS in pcDNA3 (Invitrogen)]. The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 [see, Suzuki et al., Hum Gene Ther (1996) 7:1883-1893; the disclosure of which is herein incorporated by reference in its entirety) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture is diluted with 400 µl of DMEM and 100 µl of the diluted mixture is added to each well. 100 µl of DMEM with 10% FCS are added to each well after a 4 hr incubation in a cell culture incubator. The following day the transfected cells are changed with 200 µl/well of DMEM with 10% FCS. Eight (8) hours later, the wells are changed to 100 µl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue #219073) can be utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP.

c. SRF-Luc Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with, e.g. 1 µM, test compound. Cells are then lysed and assayed for luciferase activity using a Luclite™ Kit (Packard, Cat. #6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

4. Intracellular IP3 Accumulation Assay (Gq-Associated Receptors)

On day 1, cells to be transfected with a G protein-coupled receptor of the invention can be plated onto 24 well plates, usually $1 \times 10^5$ cells/well (although his number can be optimized). On day 2 cells can be transfected by first mixing 0.25 µg DNA (e.g., pCMV vector; pCMV vector with receptor cDNA, etc.) in 50 µl serum free DMEM/well and 2 µl lipofectamine in 50 µl serum free DMEM/well. The solutions are gently mixed and incubated for 15-30 min at room temperature. Cells are washed with 0.5 ml PBS and 400 µl of serum free media is mixed with the transfection media and added to the cells. The cells are then incubated for 3-4 hrs at 37° C./5% $CO_2$ and then the transfection media is removed and replaced with 1 ml/well of regular growth media. On day 3 the cells are labeled with $^3$H-myo-inositol. Briefly, the media is removed and the cells are washed with 0.5 ml PBS. Then 0.5 ml inositol-free/serum free media (GIBCO BRL) is added/well with 0.25 µCi of $^3$H-myo-inositol/well and the cells are incubated for 16-18 hrs o/n at 37° C./5% $CO_2$. On Day 4 the cells are washed with 0.5 ml PBS and 0.45 ml of assay medium is added containing inositol-free/serum free media 10 µM pargyline 10 mM lithium chloride or 0.4 ml of assay medium and 50 µl of 10× Test Compound to final concentration of 10 µM. The cells are then incubated for 30 min at 37° C. The cells are then washed with 0.5 ml PBS and 200 µl of fresh/ice cold stop solution (1M KOH; 18 mM Na-borate; 3.8 mM EDTA) is added/well. The solution is kept on ice for 5-10 min or until cells were lysed and then neutralized by 200 µl of fresh/ice cold neutralization sol. (7.5 HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 WN and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Example 4

Fluorometric Imaging Plate Reader (FLIPR) Assay for the Measurement of Intracellular Calcium Concentration (e.g., Gq-Associated Receptors)

Target Receptor (experimental) and pCMV (negative control) stably transfected cells from respective clonal lines are seeded into poly-D-lysine pretreated 96-well plates (Becton-Dickinson, #356640) at $5.5 \times 10^4$ cells/well with complete culture medium (DMEM with 10% FBS, 2 mM L-glutamine, 1 mM sodium pyruvate) for assay the next day. To prepare Fluo4-AM (Molecular Probe, #F14202) incubation buffer stock, 1 mg Fluo4-AM is dissolved in 467 µl DMSO and 467 µl Pluoronic acid (Molecular Probe, #P3000) to give a 1 mM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 µl of 4 µM Fluo4-AM/2.5 mM Probenicid (Sigma, #P8761)/20 mM HEPES/complete medium at pH 7.4. Incubation at 37° C./5% CO2 is allowed to proceed for 60 min.

After the 1 hr incubation, the Fluo4-AM incubation buffer is removed and the cells are washed 2× with 100 µl wash buffer. In each well is left 100 µl wash buffer. The plate is returned to the incubator at 37° C./5% CO2 for 60 min.

FLIPR (Fluorometric Imaging Plate Reader; Molecular Device) is programmed to add 50 µl candidate compound on the 30th second and to record transient changes in intracellular calcium concentration ([Ca2+]) evoked by the candidate compound for another 150 seconds. Total fluorescence change counts are used to determine agonist activity using the FLIPR software. The instrument software normalizes the fluorescent reading to give equivalent initial readings at zero.

In some embodiments, the cells comprising Target Receptor further comprise Gα15, Gα16, or the chimeric Gq/Gi alpha unit.

Although the foregoing provides a FLIPR assay for agonist activity using stably transfected cells, a person of ordinary skill in the art would readily be able to modify the assay in order to characterize antagonist activity. The person of ordinary skill in the art would also readily appreciate that, alternatively, transiently transfected cells could be used.

Example 5

MAP Kinase Assay

MAP kinase (mitogen activated kinase) may be monitored to evaluate receptor activation. MAP kinase can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilin Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P is a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then be aspirated through the filter, which retains, the phosphorylated myelin basic protein. The filter is washed and counted for $^{32}$P by liquid scintillation counting.

Example 6

Melanophore Technology

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRs. This method can be conducted by introducing test cells of a pigment cell line capable of dispersing or aggregating their pigment in response to a specific stimulus and expressing an exogenous clone coding for the GPCR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods will be followed according to the disclosure of U.S. Pat. No. 5,462,856 and U.S. Pat. No. 6,051,386. These patent disclosures are hereby incorporated by reference in their entirety.

The cells are plated in e.g. 96-well plates (one receptor per plate). 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7× L-15 (Gibco). After one hour, the cells in serum-free media remain in a pigment-dispersed state while the melatonin-treated cells are in a pigment-aggregated state. At this point, the cells are treated with a dose response of a test/candidate compound. If the plated GPCRs bind to the test/candidate compound, the melanophores would be expected to undergo a color change in response to the compound. If the receptor were either a Gs or Gq coupled receptor, then the melatonin-aggregated melanophores would undergo pigment dispersion. In contrast, if the receptor was a Gi-coupled receptor, then the pigment-dispersed cells would be expected to undergo a dose-dependent pigment aggregation.

Example 7

Radiolabeled Compound

In certain embodiments, a compound known to be a ligand of a G protein-coupled receptor of the invention is radiolabeled. A radiolabeled compound as described herein can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor. Suitable radionuclides that may be incorporated in compounds of the present invention include but are not limited to $^3$H (also written as T), $^{11}$C, $^{14}$C, $^{18}$F, $^{125}$I, $^{82}$Br, $^{123}$I, $^{124}$I, $^{125}$I, $^{131}$I, $^{75}$Br, $^{76}$Br, $^{15}$O, $^{13}$N, $^{35}$S and $^{77}$Br. Compounds that incorporate $^3$H, $^{14}$C, $^{125}$I, $^{131}$I, $^{35}$S or $^{82}$Br will generally be most useful.

It is understood that a "radiolabelled" compound" is a compound that has incorporated at least one radionuclide. In some embodiments, the radionuclide is selected from the group consisting of $^3$H, $^{14}$C, $^{125}$I, $^{35}$S and $^{82}$Br. In some embodiments, the radionuclide $^3$H or $^{14}$C. Moreover, it should be understood that all of the atoms represented in the compounds known to be ligands of a G protein-coupled receptor of the invention can be either the most commonly occurring isotope of such atoms or the more scarce radioisotope or nonradioactive isotope.

Synthetic methods for incorporating radioisotopes into organic compounds including those applicable to those compounds known to be ligands of a G protein-coupled receptor of the invention are well known in the art and include incorporating activity levels of tritium into target molecules include: A. Catalytic Reduction with Tritium Gas—This procedure normally yields high specific activity products and requires halogenated or unsaturated precursors. B. Reduction with Sodium Borohydride [$^3$H]—This procedure is rather inexpensive and requires precursors containing reducible functional groups such as aldehydes, ketones, lactones, esters, and the like. C. Reduction with Lithium Aluminum Hydride [$^3$H]—This procedure offers products at almost theoretical specific activities. It also requires precursors containing reducible functional groups such as aldehydes, ketones, lactones, esters, and the like. D. Tritium Gas Exposure Labeling—This procedure involves exposing precursors containing exchangeable protons to tritium gas in the presence of a suitable catalyst. E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for high specific activity, such as about 80-87 Ci/mmol.

Synthetic methods for incorporating activity levels of $^{125}$I into target molecules include: A. Sandmeyer and like reactions—This procedure transforms an aryl or heteroaryl amine into a diazonium salt, such as a tetrafluoroborate salt, and subsequently to $^{125}$I labelled compound using Na$^{125}$I. A represented procedure was reported by Zhu, D.-G. and co-workers in *J. Org. Chem.* 2002, 67, 943-948. B. Ortho $^{125}$Iodination of phenols—This procedure allows for the incorporation of $^{125}$I at the ortho position of a phenol as reported by Collier, T. L. and co-workers in *J. Labelled Compd Radiopharm.* 1999, 42, S264-S266. C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labelled Compd Radiopharm.* 2001, 44, S280-S282.

The foregoing techniques are intended to be illustrative and not limiting. Other techniques for radiolabeling a compound known to be a ligand of a G protein-coupled receptor of the invention are well known to the skilled artisan.

Example 8

Receptor Binding Assay

A test compound can be evaluated for its ability to reduce formation of the complex between a compound known to be a ligand of a G protein-coupled receptor of the invention and the receptor. In certain embodiments, the known ligand is radiolabeled. The radiolabeled known ligand can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor.

Assay Protocol for Detecting the Complex Between a Compound Known to be a Ligand of a G Protein-Coupled Receptor of the Invention and the Receptor A. Preparation of the Receptor 293 cells are transiently transfected with 10 ug expression vector comprising a polynucleotide encoding a G protein-coupled receptor of the invention using 60 ul Lipofectamine (per 15-cm dish). The transiently transfected cells are grown in the dish for 24 hours (75% confluency) with a media change and removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM MgCl$_2$, 100 mM NaCl, pH 7.4) added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM MgCl$_2$, and 1 mM EDTA; 5-50 ug protein) is added to 96-well polyproylene microtiter plates followed by addition of 100 ul of assay buffer and 50 ul of a radiolabeled known ligand. For nonspecific binding, 50 ul of assay buffer is added instead of 100 ul and an additional 50 ul of 10 uM said known ligand which is not radiolabeled is added before 50 ul of said radiolabeled known ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For determining whether less of the complex between said radiolabeled known ligand and said receptor is formed in the presence of a test compound, instead of adding 100 ul of assay buffer, 100 ul of appropriately diluted said test compound is added to appropriate wells followed by addition of 50 ul of said radiolabled known ligand.

A level of specific binding of the radiolabled known ligand in the presence of the test compound less than a level of specific binding of the radiolabeled known ligand in the absence of the test compound is indicative of less of the complex between said radiolabeled known ligand and said receptor being formed in the presence of the test compound than in the absence of the test compound.

Example 9

BRS-3 Increases Intracellular IP3 Accumulation

COS-7 cells were transiently transfected with pCMV expression vector containing cDNA encoding endogenous human BRS-3 or with pCMV vector alone. Intracellular IP3 accumulation was read out as accumulation of total inositol phosphates.

COS-7 cells were plated at 10,000 cells per well in a 96-well plate and allowed to attach overnight. The COS-7 cells were then transfected in triplicate with 0.5 or 1.3 ng/well BRS-3/pCMV or with 13 ng/well empty pCMV, using Lipofectamine™ 2000 (Invitrogen #11668-027). After about 15 h, the transfected COS-7 cells were returned to complete medium (DMEM containing 10% FBS, 1% L-glutamine, and 1.5 g/L sodium bicarbonate) and cell culture was continued at 37° C. for about 8 hours.

The COS-7 cells were used in IP3 assay about 24 h post-transfection as described here. The complete medium was replaced with 100 μl inositol-free medium (Invitrogen/Gibco formula 02-5092EA; DMEM containing D-glucose, L-glutamine, phenol red, and pyridoxine HCl, and without inositol, sodium bicarbonate, and sodium pyruvate) supplemented with 1.5 g/L sodium bicarbonate and 4 Ci/ml [$^3$H] myo-inositol (Perkin Elmer Life Sciences), and the cells were allowed to incubate for about 15 h at 37° C. The medium was then removed by aspiration and replaced with IP3 medium (inositol-free medium as above supplemented with 10 μM pargyline and 10mM lithium chloride), and the cells were incubated for 3 hours at 37° C. (To screen a test compound as a BRS-3 agonist, the test compound would be included in this 3 h incubation.) Following incubation, the medium was removed by aspiration and replaced with buffer containing ice cold 0.1M formic acid. The plates were then frozen overnight at −80° C. to achieve complete cell lysis following an initial 30 min incubation on dry ice.

Following complete cell lysis, the assay plates were thawed in a 37° C. oven. The thawed contents were then transferred to 96-well filter plates (Millipore, Multiscreen) pre-loaded with resin (Biorad, AG1-X8 100-200 mesh, formate form). The plate was filtered using a vacuum manifold and the resin was washed multiple times with water. An elution buffer was then applied (200 μl, 1.0M ammonium formate/0.1M formic acid) and the resulting eluent was collected, under vacuum, in a 96-well collection plate. Aliquots of the eluent (200 μl) were transferred to scintillation vials containing 4 ml scintillation fluid and counted on a scintillation counter (Perkin Elmer Life Sciences, Optiphase Supermix or Hi-Safe 3).

BRS-3 was found to exhibit a detectable level of constitutive activity and to increase the level of IP3 accumulation in COS-7 cells. See FIG. 1. Analogous results were obtained using 293 cells (not shown).

Example 10

RT-PCR Analysis of BRS-3 Expression in GLUTag Cells

RT-PCR was used to determine BRS-3 expression in GLUTag cells. GLUTag is a GLP-1 producing mouse enteroendocrine L-cell line [Brubaker et al., Endocrinology (1998) 139:4108-4114].

BRS-3 expression in GLUTag cells was evaluated by RT-PCR using the following primers:

```
                                    (SEQ ID NO: 5; sense)
5'-TCCCGCTCTCGATTATCTCTGTCT-3'
and
                                    (SEQ ID NO: 6; antisense)
5'-TCCTCTCCCTTCTTGGCACTACTG-3'.
```

PCR primers SEQ ID NO:5 and SEQ ID NO:6 were chosen so as to amplify BRS-3 across an intron, such that the amplification product for cDNA (508 bp) is easily distinguishable from that for genomic DNA.

Total RNA was isolated from GLUTag cells using Trizol Reagent purchased from Invitrogen. The cDNA synthesis was performed by using a cDNA Synthesis kit from Bio-Rad (iScript™). PCR was performed using Taq Supermix (Invitrogen) in a 50 μl reaction mixture containing 2 μl cDNA and 100 ng of each primer. Control reactions included a no-template control and a mouse genomic DNA template control. Samples were placed in a thermal cycler and incubated at 94° C. for 5 minutes, followed by 30 cycles of [30 seconds at 94° C., 30 seconds at 57.5° C., and 1 minute at 72° C.], and a final incubation of 72° C. for 10 minutes. 5 μl of each PCR reaction product was then analyzed on a 1%/TAE Agarose Gel.

GLUTag cells were found to express BRS-3. See FIG. 2.

Example 11

Effect of BRS-3 Agonist on Intracellular IP3 Accumulation in GLUTag Cells

GLUTag is a GLP-1 producing mouse enteroendocrine L-cell line [Brubaker et al., Endocrinology (1998) 139:4108-4114]. The effect of BRS-3 agonist on the level of intracellular IP3 accumulation in GLUTag cells is determined.

IP3 assay in GluTag cells is carried out as described in Example 9, supra. The GLUTag cells are incubated with or without BRS-3 agonist during the 3 h incubation in IP3 medium. In certain embodiments, the BRS-3 agonist is selected from the left column of Table B.

BRS-3 agonist is found to increase intracellular IP3 accumulation in GLUTag cells.

Example 12

Effect of BRS-3 Agonist on Stimulation of GLP-1 Secretion in GLUTag Cells

GLUTag is a GLP-1 producing mouse enteroendocrine L-cell line [Brubaker et al., Endocrinology (1998) 139:4108-4114]. The effect of BRS-3 agonist on stimulation of GLP-1 secretion in GLUTag cells is determined.

GLUTag cells are plated in 24-well plates on day one in complete culture medium (DMEM/10% FBS). On day two the culture medium is replaced with a low glucose medium (DMEM/3 mM Glucose/10% FBS). On day three cells are washed twice with 1×PBS. The washed GLUTag cells are stimulated with BRS-3 agonist at various concentrations (from about 1 nM to about 10 µM, by way of illustration and not limitation) or with forskolin (1 µM) as a positive control in serum free DMEM with 15 mM glucose for one hour at 37° C. and 5% $CO_2$ in a tissue culture incubator. The supernatants are then collected and clarified by centrifugation at 500 g and 4° C. for 5 minutes. GLP-1 released into the supernatant is determined by ELISA using reagents purchased from LINCO Research Laboratory [Glucagon-Like Peptide-1 (Active) ELISA Kit. Cat. #EGLP-35K].

GLUTag cells are found to secrete GLP-1 when stimulated with BRS-3 agonist.

Example 13

Effect of BRS-3 Agonist and DPP-IV Inhibitor in Lowering an Elevated Blood Glucose Level in Oral Glucose Tolerance Test (oGTT) in Mice Oral glucose tolerance test (oGTT) in mice is carried out as described here.

In mouse oGTT assay, a therapeutically effective amount is typically that amount of drug which will create an AUC inhibition above 30%, whereas a therapeutically ineffective amount is typically an amount of drug which will create an AUC inhibition less than or equal to 30%.

Overnight fasted mice (n=6 mice per treatment) are administered via oral gavage with vehicle (PET), a BRS-3 agonist [e.g., at a dose between about 0.1 mkg to about 1 mkg (milligram compound per kilogram of body weight) which is therapeutically effective when used alone], a DPP-IV inhibitor [e.g., at a dose between about 0.1 mkg to about 1 mkg which is therapeutically ineffective when used alone], or a combination of the BRS-3 agonist and the DPP-IV inhibitor (e.g., at the foregoing therapeutically ineffective doses). Thirty minutes later, a glucose bolus (3 gram/kg) is then delivered per orally. Plasma glucose levels are determined at about 20 min intervals over a two hour period using blood (~5 µl) collected from tail nick and a glucose meter. Glycemic excursion curve is graphed based on data from 6 mice and is given in mean values +/−SEM. Area Under Curve (AUC) of the glycemic excursion is calculated for each mouse and AUC inhibition (%) is determined.

The combination of BRS-3 agonist and DPP-IV inhibitor is found to produce a synergistic AUC inhibition compared to that of BRS-3 agonist alone or DPP-IV inhibitor alone.

The combination of an amount of a BRS-3 agonist and a DPP-IV inhibitor is found to produce an AUC inhibition greater than the inhibition given by the amount of the BRS-3 agonist alone and the inhibition given by the amount of the DPP-IV inhibitor alone.

Example 14

Combination of BRS-3 Agonist and DPP-IV Inhibitor for Treating or Preventing Diabetes and Conditions Related Thereto A BRS-3 agonist in accordance with the present invention is selected. A DPP-IV inhibitor in accordance with the present invention is selected.

Titration of the BRS-3 agonist with respect to percent inhibition of Area Under Curve (AUC) in mouse oral glucose tolerance test (oGTT) is determined across a dose range from about 0.01 mkg (milligram compound per kilogram of body weight) to about 100 mkg. See Example 13, supra. A dose of the BRS-3 agonist producing an AUC inhibition of glycemic excursion of about 15-20% is chosen. Typically, a dose of BRS-3 agonist producing an AUC inhibition 30% or less is therapeutically ineffective in this mouse model.

Titration of the DPP-IV inhibitor with respect to percent inhibition of Area Under Curve (AUC) in mouse oral glucose tolerance test (oGTT) is determined across a dose range from about 0.01 mkg (milligram compound per kilogram of body weight) to about 100 mkg. See Example 13, supra. A dose of the DPP-IV inhibitor producing an AUC inhibition of glycemic excursion of about 15-20% is chosen. Typically, a dose of DPP-IV inhibitor producing an AUC inhibition 30% or less is therapeutically ineffective in this mouse model.

The AUC inhibition of glycemic excursion produced by the combination of the chosen dose of the BRS-3 agonist and the chosen dose of the DPP-IV inhibitor is determined in mouse oGTT assay. Therapeutic efficacy of the combination of the BRS-3 agonist and the DPP-IV inhibitor is determined Typically, an amount of the combination producing an AUC inhibition above 30% is therapeutically effective in this mouse model. Synergism between the BRS-3 agonist and the DPP-IV inhibitor is determined.

Data obtained from this mouse model can be used to formulate a range of dosage for use in humans. In general, one skilled in the art understands how to extrapolate in vivo data obtained in an animal model system to another, such as a human. A combination of BRS-3 agonist and DPP-IV inhibitor in accordance with the present invention is useful in treating or preventing diabetes and conditions related thereto.

It is understood that the foregoing is intended to be illustrative and not limiting.

Example 15

Effect of BRS-3 Agonist and DPP-IV Inhibitor in Increasing a Blood GLP-1 Level After Glucose Challenge in Mice C57blk/6 male mice (8 weeks of age) are fasted for 18 hours, and randomly assigned into twelve groups with n=6 for each group. Mice are administered per orally with vehicle (PET), a BRS-3 agonist [e.g., at a dose between about 0.1 mkg to about 1 mkg (milligram compound per kilogram of body weight) which is therapeutically effective when used alone], a DPP-IV inhibitor [e.g., at a dose between about 0.1 mkg to about 1 mkg which is therapeutically ineffective when used alone], or a combination of the BRS-3 agonist and the DPP-IV inhibitor (e.g., at the foregoing therapeutically ineffective doses). Thirty minutes after treatment, a glucose bolus at 3 g/kg is delivered per orally, and plasma is collected at 0 minute (no glucose bolus), and at 2 minutes and 5 minutes after glucose bolus. Plasma GLP-1 levels are determined by using a GLP-1 ELISA kit purchased from Linco Research Laboratory [Glucagon-Like Peptide-1 (Active) ELISA kit, Catalog #EGLP-35K].

Administration of a BRS-3 agonist together with a DPP-IV inhibitor is found to produce a synergistic effect in increasing a blood GLP-1 level.

Administration of an amount of a BRS-3 agonist in combination with an amount of a DPP-IV inhibitor is found to produce an effect in increasing a blood GLP-1 level greater than the effect given by the amount of the BRS-3 agonist alone and the effect given by the amount of the DPP-IV inhibitor alone.

Example 16

Yeast Reporter Assay for BRS-3 Agonist Activity

The yeast cell-based reporter assays have previously been described in the literature (e.g., see Miret et al, J Biol Chem (2002) 277:6881-6887; Campbell et al, Bioorg Med Chem Lett (1999) 9:2413-2418; King et al, Science (1990) 250:121-123; WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally, the endogenous yeast alpha-cell GPCR, Ste3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic readout.

Yeast cells are transformed by an adaptation of the lithium acetate method described by Agatep et al (Agatep et al, 1998, Transformation of Saccharomyces cerevisiae by the lithium acetate/single-stranded carrier DNA/polyethylene glycol (LiAc/ss-DNA/PEG) protocol. Technical Tips Online, Trends Journals, Elsevier). Briefly, yeast cells are grown overnight on yeast tryptone plates (YT). Carrier single-stranded DNA (10 μg), 2 μg of each of two Fus1p-LacZ reporter plasmids (one with URA selection marker and one with TRP), 2 μg of BRS-3 (e.g., human receptor) in yeast expression vector (2 μg origin of replication) and a lithium acetate/polyethylene glycol/TE buffer is pipetted into an Eppendorf tube. The yeast expression plasmid containing the receptor/no receptor control has a LEU marker. Yeast cells are inoculated into this mixture and the reaction proceeds at 30° C. for 60 min. The yeast cells are then heat-shocked at 42° C. for 15 min. The cells are then washed and spread on selection plates. The selection plates are synthetic defined yeast media minus LEU, URA and TRP (SD-LUT). After incubating at 30° C. for 2-3 days, colonies that grow on the selection plates are then tested in the LacZ assay.

In order to perform fluorimetric enzyme assays for β-galactosidase, yeast cells carrying the subject BRS-3 receptor are grown overnight in liquid SD-LUT medium to an unsaturated concentration (i.e. the cells are still dividing and have not yet reached stationary phase). They are diluted in fresh medium to an optimal assay concentration and 90 μl of yeast cells are added to 96-well black polystyrene plates (Costar). Test compounds, dissolved in DMSO and diluted in a 10% DMSO solution to 10× concentration, are added to the plates and the plates placed at 30° C. for 4 h. After 4 h, the substrate for the β-galactosidase is added to each well. In these experiments, Fluorescein di (β-D-galactopyranoside) is used (FDG), a substrate for the enzyme that releases fluorescein, allowing a fluorimetric read-out. 20 μl per well of 500 μM FDG/2.5% Triton X100 is added (the detergent is necessary to render the cells permeable). After incubation of the cells with the substrate for 60 min, 20 μl per well of 1M sodium carbonate is added to terminate the reaction and enhance the fluorescent signal. The plates are then read in a fluorimeter at 485/535 nm.

An increase in fluorescent signal pigment dispersion in BRS-3-transformed yeast cells over that in yeast cells transformed with empty vector is indicative of a test compound being a compound that stimulates BRS-3 receptor functionality.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A method of identifying a Glucagon-like Peptide-1 (GLP-1) secretagogue or a compound useful for treating a condition ameliorated by increasing a GLP-1 level, comprising:
   (a) contacting a Bombesin Receptor Subtype-3 (BRS-3) agonist in vitro with a mammalian enteroendocrine cell; and
   (b) determining whether the BRS-3 agonist stimulates GLP-1 secretion from the mammalian enteroendocrine cell;
   wherein the ability of the BRS-3 agonist to stimulate GLP-1 secretion from the mammalian enteroendocrine cell is indicative of the agonist being a GLP-1 secretagogue or a compound useful for treating a condition ameliorated by increasing a GLP-1 level.

2. The method of claim 1, wherein the mammalian enteroendocrine cell is a GLUTag enteroendocrine L-cell line.

3. The method of claim 1, wherein the condition ameliorated by increasing a GLP-1 level is selected from the group consisting of diabetes, a condition related to diabetes, myocardial infarction, learning impairment, memory impairment, and a neurodegenerative disorder.

4. The method of claim 1, wherein the method is for identifying a GLP-1 secretagogue.

5. The method of claim 1, wherein the BRS-3 agonist is an agonist of human BRS-3.

6. The method of claim 1, wherein the BRS-3 agonist is a small molecule.

7. The method of claim 1, wherein the BRS-3 agonist is orally active.

8. The method of claim 1, wherein the selective BRS-3 agonist has a selectivity for BRS-3 over gastric-releasing peptide receptor of at least 10-fold.

9. The method of claim 1, wherein the selective BRS-3 agonist has a selectivity for BRS-3 over neuromedin B receptor of at least 10-fold.

10. The method of claim 1, wherein the BRS-3 agonist is a partial agonist.

11. The method of claim 1, further comprising formulating the BRS-3 agonist that is identified as being a GLP-1 secretagogue or a compound useful for treating a condition ameliorated by increasing a GLP-1 level as a pharmaceutical composition.

12. The method of claim 1, wherein the BRS-3 agonist has an EC50 of less than 10 μM.

13. The method of claim 1, wherein the BRS-3 agonist has an EC50 of less than 1 μM.

14. The method of claim 1, wherein the BRS-3 agonist has an EC50 of less than 100 nM.

15. The method of claim 1, wherein determining whether the BRS-3 agonist stimulates GLP-1 secretion from the mammalian enteroendocrine cell comprises performing an enzyme-linked immunosorbent assay (ELISA).

16. A method of identifying a Glucagon-like Peptide-1 (GLP-1) secretagogue or a compound useful for treating a condition ameliorated by increasing a GLP-1 level, comprising:
   (a) determining a GLP-1 level in a biological sample obtained from a mammal, the mammal having been administered with a selective Bombesin Receptor Subtype-3 (BRS-3) agonist;
   wherein the ability of the BRS-3 agonist to increase a GLP-1 level in the mammal is indicative of the agonist being a GLP-1 secretagogue or a compound useful for treating a condition ameliorated by increasing a GLP-1 level.

17. The method of claim 16, wherein the mammal is a non-human mammal.

18. The method of claim 16, wherein the mammal is a human.

19. The method of claim 16, wherein the condition ameliorated by increasing a GLP-1 level is selected from the group consisting of diabetes, a condition related to diabetes, myocardial infarction, learning impairment, memory impairment, and a neurodegenerative disorder.

20. The method of claim 16, wherein the method is for identifying a GLP-1 secretagogue.

21. The method of claim 16, wherein the BRS-3 agonist is an agonist of human BRS-3.

22. The method of claim 16, wherein the BRS-3 agonist is a small molecule.

23. The method of claim 16, wherein the BRS-3 agonist is orally active.

24. The method of claim 16, wherein the selective BRS-3 agonist has a selectivity for BRS-3 over gastric-releasing peptide receptor of at least 10-fold.

25. The method of claim 16, wherein the selective BRS-3 agonist has a selectivity for BRS-3 over neuromedin B receptor of at least 10-fold.

26. The method of claim 16, wherein the BRS-3 agonist is a partial agonist.

27. The method of claim 16, further comprising formulating the BRS-3 agonist that is identified as being a GLP-1 secretagogue or a compound useful for treating a condition ameliorated by increasing a GLP-1 level as a pharmaceutical composition.

28. The method of claim 16, wherein the BRS-3 agonist has an EC50 of less than 10 μM.

29. The method of claim 16, wherein the BRS-3 agonist has an EC50 of less than 1 μM.

30. The method of claim 16, wherein the BRS-3 agonist has an EC50 of less than 100 nM.

31. The method of claim 16, wherein determining the GLP-1 level in the biological sample obtained from the mammal comprises performing an ELISA.

32. The method of claim 31, wherein the biological sample is a blood sample or a plasma sample.

33. The method of claim 16, wherein the biological sample is a blood sample or a plasma sample.

34. A method of identifying a Glucagon-like Peptide-1 (GLP-1) secretagogue or a compound useful for treating a condition ameliorated by increasing a GLP-1 level, comprising:
 (a) administering a mammal with a selective Bombesin Receptor Subtype-3 (BRS-3) agonist; and
 (b) determining a GLP-1 level in a biological sample obtained from the mammal,
 wherein the ability of the BRS-3 agonist to increase a GLP-1 level in the mammal is indicative of the agonist being a GLP-1 secretagogue or a compound useful for treating a condition ameliorated by increasing a GLP-1 level.

35. The method of claim 34, wherein the mammal is a non-human mammal.

36. The method of claim 34, wherein the mammal is a human.

37. The method of claim 34, wherein the condition ameliorated by increasing a GLP-1 level is selected from the group consisting of diabetes, a condition related to diabetes, myocardial infarction, learning impairment, memory impairment, and a neurodegenerative disorder.

38. The method of claim 34, wherein the method is for identifying a GLP-1 secretagogue.

39. The method of claim 34, wherein the BRS-3 agonist is an agonist of human BRS-3.

40. The method of claim 34, wherein the BRS-3 agonist is a small molecule.

41. The method of claim 34, wherein the BRS-3 agonist is orally active.

42. The method of claim 34, wherein the selective BRS-3 agonist has a selectivity for BRS-3 over gastric-releasing peptide receptor of at least 10-fold.

43. The method of claim 34, wherein the selective BRS-3 agonist has a selectivity for BRS-3 over neuromedin B receptor of at least 10-fold.

44. The method of claim 34, wherein the BRS-3 agonist is a partial agonist.

45. The method of claim 34, further comprising formulating the BRS-3 agonist that is identified as being a GLP-1 secretagogue or a compound useful for treating a condition ameliorated by increasing a GLP-1 level as a pharmaceutical composition.

46. The method of claim 34, wherein the BRS-3 agonist has an EC50 of less than 10 µM.

47. The method of claim 34, wherein the BRS-3 agonist has an EC50 of less than 1 µM.

48. The method of claim 34, wherein the BRS-3 agonist has an EC50 of less than 100 nM.

49. The method of claim 34, wherein determining the GLP-1 level in the biological sample obtained from the mammal comprises performing an ELISA.

50. The method of claim 49, wherein the biological sample is a blood sample or a plasma sample.

51. The method of claim 34, wherein the biological sample is a blood sample or a plasma sample.

52. A method of determining whether a selective Bombesin Receptor Subtype-3 (BRS-3) agonist increases Glucagon-like Peptide-1 (GLP-1) secretion from a mammalian enteroendocrine cell, comprising:
 (a) contacting the BRS-3 agonist with the mammalian enteroendocrine cell; and
 (b) determining GLP-1 secretion from the mammalian enteroendocrine cell.

* * * * *

SEQUENCE LISTING

```
<160> NUMBER OF SEQ ID NOS: 6

<210> SEQ ID NO 1
<211> LENGTH: 1200
<212> TYPE: DNA
<213> ORGANISM: Homo sapien

<400> SEQUENCE: 1
atggctcaaa ggcagcctca ctcacctaat cagactttaa tttcaatcac aaatgacaca      60
gaatcatcaa gctctgtggt ttctaacgat aaacaaaata aaggatggag cggggacaac     120
tctccaggaa tagaagcatt gtgtgccatc tatattactt atgctgtgat catttcagtg     180
```

-continued

```
ggcatccttg gaaatgctat tctcatcaaa gtcttttca agaccaaatc catgcaaaca      240
gttccaaata ttttcatcac cagcctggct tttggagatc tttactcct gctaacttgt      300 gtgccagtgg atgcaactca ctaccttgca gaaggatggc tgttcggaag aattggttgt      360
aaggtgctct ctttcatccg gctcacttct gttggtgtgt cagtgttcac attaacaatt      420
ctcagcgctg acagatacaa ggcagttgtg aagccacttg agcgacagcc ctccaatgcc      480
atcctgaaga cttgtgtaaa agctggctgc gtctggatcg tgtctatgat atttgctcta      540
cctgaggcta tattttcaaa tgtatacact tttcgagatc ccaataaaaa tatgacattt      600
gaatcatgta cctcttatcc tgtctctaag aagctcttgc aagaaataca ttctctgctg      660
tgcttcttag tgttctacat tattccactc tctattatct ctgtctacta ttccttgatt      720
gctaggaccc tttacaaaag caccctgaac atacctactg aggaacaaag ccatgcccgt      780
aagcagattg aatcccgaaa agaattgcc agaacggtat tggtgttggt ggctctgttt      840
gccctctgct ggttgccaaa tcacctcctg tacctctacc attcattcac ttctcaaacc      900
tatgtagacc cctctgccat gcatttcatt ttcaccattt tctctcgggt tttggcttc      960 agcaattctt gcgtaaaccc ctttgctctc tactggctga gcaaaagctt ccagaagcat     1020
tttaaagctc agttgttctg ttgcaaggcg gagcggcctg agcctcctgt tgctgacacc     1080
tctcttacca ccctggctgt gatgggaacg gtcccgggca ctgggagcat acagatgtct     1140
gaaattagtg tgacctcgtt cactgggtgt agtgtgaagc aggcagagga cagattctag    1200
```

<210> SEQ ID NO 2
<211> LENGTH: 399
<212> TYPE: PRT
<213> ORGANISM: homo sapien

<400> SEQUENCE: 2

```
Met Ala Gln Arg Gln Pro His Ser Pro Asn Gln Thr Leu Ile Ser Ile
1               5                   10                  15

Thr Asn Asp Thr Glu Ser Ser Ser Val Val Ser Asn Asp Asn Thr
            20                  25                  30

Asn Lys Gly Trp Ser Gly Asp Asn Ser Pro Gly Ile Glu Ala Leu Cys
        35                  40                  45

Ala Ile Tyr Ile Thr Tyr Ala Val Ile Ile Ser Val Gly Ile Leu Gly
    50                  55                  60

Asn Ala Ile Leu Ile Lys Val Phe Phe Lys Thr Lys Ser Met Gln Thr
65                  70                  75                  80

Val Pro Asn Ile Phe Ile Thr Ser Leu Ala Phe Gly Asp Leu Leu Leu
                85                  90                  95

Leu Leu Thr Cys Val Pro Val Asp Ala Thr His Tyr Leu Ala Glu Gly
            100                 105                 110

Trp Leu Phe Gly Arg Ile Gly Cys Lys Val Leu Ser Phe Ile Arg Leu
        115                 120                 125

Thr Ser Val Gly Val Ser Val Phe Thr Leu Thr Ile Leu Ser Ala Asp
    130                 135                 140

Arg Tyr Lys Ala Val Val Lys Pro Leu Glu Arg Gln Pro Ser Asn Ala
145                 150                 155                 160

Ile Leu Lys Thr Cys Val Lys Ala Gly Cys Val Trp Ile Val Ser Met
                165                 170                 175

Ile Phe Ala Leu Pro Glu Ala Ile Phe Ser Asn Val Tyr Thr Phe Arg
            180                 185                 190
```

```
Asp Pro Asn Lys Asn Met Thr Phe Glu Ser Cys Thr Ser Tyr Pro Val
        195                 200                 205
Ser Lys Lys Leu Leu Gln Glu Ile His Ser Leu Leu Cys Phe Leu Val
    210                 215                 220
Phe Tyr Ile Ile Pro Leu Ser Ile Ser Val Tyr Ser Leu Ile
225                 230                 235                 240
Ala Arg Thr Leu Tyr Lys Ser Thr Leu Asn Ile Pro Thr Glu Glu Gln
                245                 250                 255
Ser His Ala Arg Lys Gln Ile Glu Ser Arg Lys Arg Ile Ala Arg Thr
            260                 265                 270
Val Leu Val Leu Val Ala Leu Phe Ala Leu Cys Trp Leu Pro Asn His
            275                 280                 285
Leu Leu Tyr Leu Tyr His Ser Phe Thr Ser Gln Thr Tyr Val Asp Pro
        290                 295                 300
Ser Ala Met His Phe Ile Phe Thr Ile Phe Ser Arg Val Leu Ala Phe
305                 310                 315                 320
Ser Asn Ser Cys Val Asn Pro Phe Ala Leu Tyr Trp Leu Ser Lys Ser
                325                 330                 335
Phe Gln Lys His Phe Lys Ala Gln Leu Phe Cys Cys Lys Ala Glu Arg
            340                 345                 350
Pro Glu Pro Pro Val Ala Asp Thr Ser Leu Thr Thr Leu Ala Val Met
        355                 360                 365
Gly Thr Val Pro Gly Thr Gly Ser Ile Gln Met Ser Glu Ile Ser Val
370                 375                 380
Thr Ser Phe Thr Gly Cys Ser Val Lys Gln Ala Glu Asp Arg Phe
385                 390                 395

<210> SEQ ID NO 3
<211> LENGTH: 30
<212> TYPE: DNA
<213> ORGANISM: Artificial
<220> FEATURE:
<223> OTHER INFORMATION: Primer

<400> SEQUENCE: 3
acagaattca gaagaaatgg ctcaaaggca                              30

<210> SEQ ID NO 4
<211> LENGTH: 30
<212> TYPE: DNA
<213> ORGANISM: Artificial
<220> FEATURE:
<223> OTHER INFORMATION: Primer

<400> SEQUENCE: 4
catggatcct tgaaaagcta gaatctgtcc                              30

<210> SEQ ID NO 5
<211> LENGTH: 24
<212> TYPE: DNA
<213> ORGANISM: Artificial
<220> FEATURE:
<223> OTHER INFORMATION: Primer

<400> SEQUENCE: 5
tcccgctctc gattatctct gtct                                    24
```

```
<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
tcctctccct tcttggcact actg                                            24
```